(12) United States Patent
Sun et al.

(10) Patent No.: US 12,115,149 B2
(45) Date of Patent: Oct. 15, 2024

(54) FORMULATIONS, METHODS, KITS, AND DOSAGE FORMS

(71) Applicant: MedRegen, LLC, Baltimore, MD (US)

(72) Inventors: Zhaoli Sun, Baltimore, MD (US); John Sun, Baltimore, MD (US); Christy Eatmon, Greenville, NC (US); Rachel Labell, Greenville, NC (US); Zhimin Liu, Greenville, NC (US); Richard Brewer, Greenville, NC (US); Isaac Agyemang, Greenville, NC (US); Mitchell Williams, Greenville, NC (US)

(73) Assignee: MedRegen, LLC, Baltimore, MD (US)

( * ) Notice: Subject to any disclaimer, the term of this patent is extended or adjusted under 35 U.S.C. 154(b) by 0 days.

(21) Appl. No.: 17/523,323

(22) Filed: Nov. 10, 2021

(65) Prior Publication Data

US 2022/0142992 A1 May 12, 2022

Related U.S. Application Data

(60) Provisional application No. 63/111,895, filed on Nov. 10, 2020.

(51) Int. Cl.
| | | |
|---|---|---|
| *A61K 31/436* | (2006.01) | |
| *A61K 9/00* | (2006.01) | |
| *A61K 31/495* | (2006.01) | |
| *A61K 47/02* | (2006.01) | |
| *A61K 47/10* | (2017.01) | |
| *A61K 47/22* | (2006.01) | |
| *A61P 11/00* | (2006.01) | |
| *A61P 29/00* | (2006.01) | |

(52) U.S. Cl.
CPC .......... *A61K 31/436* (2013.01); *A61K 9/0019* (2013.01); *A61K 31/495* (2013.01); *A61K 47/02* (2013.01); *A61K 47/10* (2013.01); *A61K 47/22* (2013.01); *A61P 11/00* (2018.01); *A61P 29/00* (2018.01)

(58) Field of Classification Search
CPC ............................ A61K 31/436; A61K 31/495
See application file for complete search history.

(56) References Cited

U.S. PATENT DOCUMENTS

| | | | |
|---|---|---|---|
| 7,029,666 B2 | 4/2006 | Bruder et al. | |
| 10,420,751 B2* | 9/2019 | Sun ...................... | A61K 38/193 |
| 11,291,657 B2* | 4/2022 | Sun ...................... | A61K 38/19 |
| 2010/0297221 A1 | 11/2010 | Coulter | |
| 2011/0318277 A1 | 12/2011 | Dalby et al. | |
| 2016/0106710 A1 | 4/2016 | Sun et al. | |
| 2018/0200232 A1 | 7/2018 | Sun et al. | |
| 2022/0184043 A1* | 6/2022 | Sun ...................... | A61K 38/193 |

FOREIGN PATENT DOCUMENTS

| | | | | |
|---|---|---|---|---|
| CN | 105727255 A | | 7/2016 | |
| WO | WO-2017011750 A1 | * | 1/2017 | .......... A61K 31/395 |
| WO | 2018/067987 A1 | | 4/2018 | |

OTHER PUBLICATIONS

FK506 (Tacrolimus) Monotherapy for Prevention of Graft-Versus-Host Disease After Histocompatible Sibling Allogeneic Bone Marrow Transplantation Blood, 87(8), 1996, 3514-3519 (Year: 1996).*
Cashen, Amanda, et al., "A Phase II Study of Plerixafor (AMD3100) plus G-CSF for Autologous Hematopoietic Progenitor Cell Mobilization in Patients with Hodgkin Lymphoma", *Biology of Blood and Marrow Transplantation*, Nov. 2008, vol. 14, No. 11, pp. 1253-1261.
International Search Report and Written Opinion for corresponding PCT International Application No. PCT/US2021/058727 dated Mar. 17, 2022.
International Preliminary Report on Patentability from counterpart International Application No. PCT/US2021/058727, dated May 25, 2023.
Extended European Search Report from corresponding EP Appln. No. 21892700.2 dated Sep. 3, 2024.

* cited by examiner

*Primary Examiner* — Sikarl A Witherspoon
(74) *Attorney, Agent, or Firm* — DLA Piper LLP (US)

(57) ABSTRACT

Embodiments of the disclosure relate generally to formulations, methods, kits, and dosage forms for improved stability comprising at least two active ingredients, AMD3100, or similar stem cell mobilizer, and Tacrolimus, or FK506 derivative or analog, and one or more excipients. The formulations may be administered as a single dose subcutaneous injection. The formulations may be useful in treating various diseases, disorders or injuries.

9 Claims, 28 Drawing Sheets

FORMULATIONS, METHODS, KITS, AND DOSAGE FORMS

TECHNICAL FIELD

Embodiments of the disclosure relate generally to formulations, methods, kits, and dosage forms of an improved pharmaceutical formulation for subcutaneous injection.

BACKGROUND

AMD3100 is a CXCR4 antagonist used for mobilization of stem cells in stem cell donors. FK506 is an immunosuppressive drug widely used at higher doses in solid organ transplantation to prevent organ rejection. Currently, Mozobil® (plerixafor, AMD3100) injection is indicated in combination with granulocyte-colony stimulating factor (G-CSF) to mobilize hematopoietic stem cells (HSCs) to the peripheral blood for collection and subsequent autologous transplantation in patients with non-Hodgkin's lymphoma (NHL) and multiple myeloma. PROGRAF (tacrolimus, FK506) is a calcineurin-inhibitor immunosuppressant indicated for the prophylaxis of organ rejection in adult and pediatric patients receiving allogeneic liver, kidney or heart transplants, in combination with other immunosuppressants. PROGRAF (tacrolimus) capsules is for oral use or PROGRAF (tacrolimus) injection is for intravenous use. Currently, PROGRAF may not be available for subcutaneous injection.

There remains a need for pharmaceutical formulations for single dose subcutaneous injection which are useful in the mobilization and recruitment of stem cells.

SUMMARY

The present disclosure relates to formulations, methods, kits, and dosage forms for treating various diseases, disorders, and/or injuries. In an embodiment, the present disclosure provides a pharmaceutical formulation comprising active pharmaceutical ingredients AMD3100 and Tacrolimus (FK506). In one embodiment, the active pharmaceutical ingredients can comprise any stem cell mobilizers similar to AMD3100. In one embodiment, the active pharmaceutical ingredients can comprise any FK506 derivatives or analogs. In one embodiment, the formulation further comprises one or more excipients. In one embodiment, the formulation is formulated as a single dose subcutaneous injection.

The present disclosure provides methods for manufacturing pharmaceutical formulations comprising AMD3100, or any stem cell mobilizers similar to AMD3100, and Tacrolimus, or any FK506 derivatives or analogs. In one embodiment, the present disclosure provides a dosage form comprising a pharmaceutical formulation comprising the active ingredients as disclosed herein and one or more excipients, wherein the pharmaceutical formulation remains stable for a predetermined time and under predetermined conditions.

In one embodiment, the present disclosure provides a method of manufacturing or stabilizing a pharmaceutical formulation. In one embodiment, the present disclosure provides a kit comprising one or more dosage forms and instructions for administering the dosage forms to a subject, wherein the dosage forms comprise a pharmaceutical formulation comprising at least two active ingredients and one or more excipients, wherein the active ingredients comprise AMD3100, or any stem cell mobilizers similar to AMD3100, and Tacrolimus (FK506), or any FK506 derivatives or analogs, wherein the dosage form remains stable for a predetermined time and under predetermined conditions.

BRIEF DESCRIPTION OF THE DRAWINGS

The foregoing summary and the following detailed description are better understood when read in conjunction with the appended drawings. Exemplary embodiments are shown in the drawings; however, it is understood that the embodiments are not limited to the specific structures depicted herein. In the drawings.

DETAILED DESCRIPTION

Figure 1A:
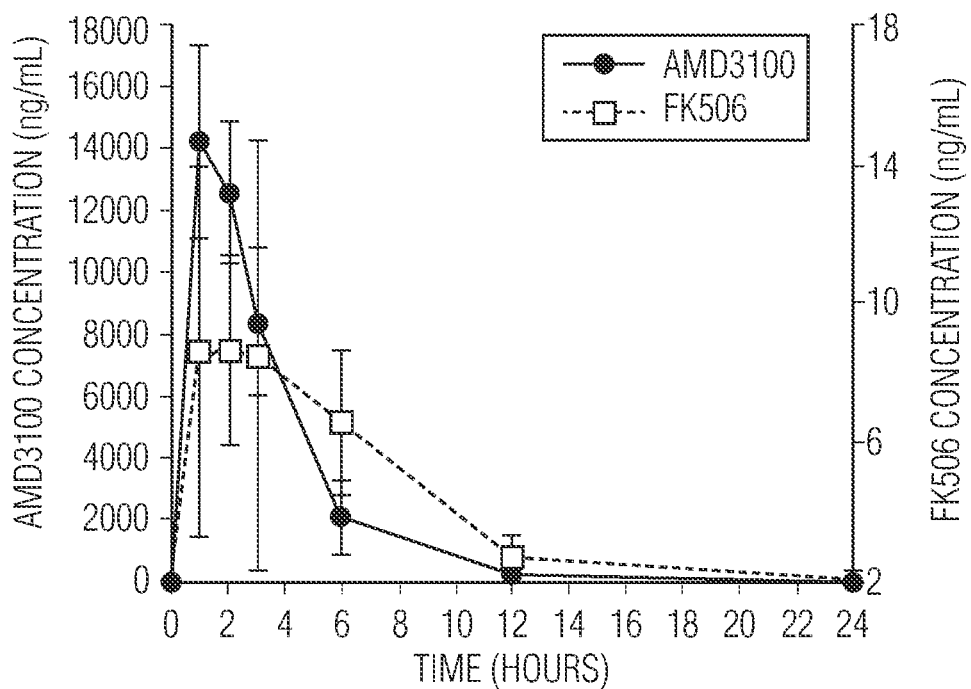
FIG. 1A shows mean AMD3100 and FK506 plasma concentrations over time on linear scales in rats, according to an exemplary embodiment of the present disclosure.

The following detailed description is exemplary and explanatory and is intended to provide further explanation of the present disclosure described herein. Other advantages, and novel features will be readily apparent to one of ordinary skill in the art from the following detailed description of the present disclosure.

In one embodiment, a pharmaceutical formulation of the disclosure comprises A "patient" or "subject" is a mammal, e.g., a human or a veterinary patient or subject, e.g., mouse, rat, guinea pig, dog, cat, horse, cow, pig, or non-human primate, such as a monkey, chimpanzee, baboon or gorilla.

In one embodiment, the term "analog" can mean a structural analog, e.g., a compound having a structure similar to that of another compound but differing from it in certain aspects, or a functional analog, e.g., a compound that has similar physical, chemical, biochemical, and/or pharmacological properties of another compound.

In one embodiment, the term "derivative" can mean a compound that is derived from a similar compound, for example by a chemical reaction.

The terms "comprise", "comprises", and "comprising" are to be interpreted inclusively rather than exclusively. The terms "consist", "consisting", and its variants, are to be interpreted exclusively, rather than inclusively.

As used herein, the term "about" means a variability of 10% from the reference given, unless otherwise specified.

The disclosure provides a pharmaceutical formulation comprising therapeutically effective amounts of AMD3100, or any stem cell mobilizers similar to AMD3100, and Tacrolimus, or any FK506 derivative or analog. In one embodiment, the formulation is formulated for single dose subcutaneous injection in a patient or subject. Surprisingly and unexpectedly, a synergism of AMD3100 (or any similar stem cell mobilizer) and low-dose tacrolimus (or any FK506 derivative or analog) (for example, one tenth of effective dosage to prevent rejection) in the mobilization and recruitment of stem cells was discovered. In one embodiment, the low-dose tacrolimus may bind to the FK506 binding protein (FKBP) but may not act on the calcineurin pathway (the mechanism for its immunosuppressive effect). This independence from any immunosuppressive effect may be confirmed by a non-immunosuppressive congener of tacrolimus that was discovered and conferred the same or similar benefits as the tacrolimus. Instead of the calcineurin pathway, the low-dose tacrolimus may act through an alternate, the bone morphogenetic protein (BMP) signaling pathway. In addition to the graft chimerism that produces allograft tolerance, stem cell mobilization and homing to damaged tissue due to combination of AMD3100 and Tacrolimus may be safe and effective for treating various diseases, disorders or injuries, for example, skin wound healing, treating IBD, preventing post-surgical peritoneal adhesions, promoting liver regeneration, improving wound healing and microvasculature in severe diabetes in animals. Given that AMD3100 is an antagonist of CXCR4, which can mobilize stem cells from bone marrow to the circulation, while Tacrolimus is an immunosuppressive drug used for preventing organ rejection, those skilled in the art would not have thought that these two unrelated drugs could have the synergy in mobilization and recruitment of stem cells. The inventors have discovered an unexpected and surprising synergistic effect based on a fixed dose combination of Tacrolimus (FK506) and AMD3100 for subcutaneous injection and have found that low dose (a non-immunosuppressive dosage) of Tacrolimus can promote stem cell recruitment to injured sites.

There have been challenges and/or difficulty in developing a combination drug comprising AMD3100 and Tacrolimus. For example, AMD3100 octahydrochloride hydrate is soluble in water at 22 mg/ml, while FK506 (Tacrolimus) has a poor solubility in water. Tacrolimus may exhibit poor aqueous solubility, P-gp efflux, and extensive presystemic metabolism, which can result in low bioavailability following oral administration. Tacrolimus can be very sensitive to temperature and pH and may degrade to form impurities with very closely related structures by rearrangement. Based on the relative insolubility of Tacrolimus in water, a suitable combination drug comprising Tacrolimus may be difficult to achieve. For example, solubility of two APIs can result in instability of FK506. About 50% of FK506 may be degraded and these degradants can reduce the synergy of the two drugs, AMD3100 and Tacrolimus, in mobilizing and recruiting stem cells in animals or subjects. The inventors have discovered a novel formulation and manufacturing process that surprisingly and unexpectedly resulted in a synergistic effect of the APIs and also increases the stability of Tacrolimus and/or the formulation. The inventors have discovered a novel formulation that includes Tacrolimus in a low dosage, for example, a dosage that can be about 15 times lower than the Tacrolimus dosage (administered orally or via intravenous injection) currently approved by the Food and Drug Administration (FDA). In addition, the novel formulation of the present disclosure can result in blood trough levels that can be undetectable when administered subcutaneously.

The disclosure provides one or more pharmaceutical formulations comprising therapeutically effective amounts of AMD3100, or any similar stem cell mobilizer, and Tacrolimus, or any FK506 derivative or analog. In one embodiment, the formulation further comprises one or more excipients. The excipients can comprise one or more of the following: solubilizing agents, penetration enhancers, emollients, solvents, salts, osmotic agents, pH adjusters, and/or water for injection.

The one or more active ingredients, for example, AMD3100 or similar stem cell mobilizer, can be in a concentration of about 1 mg/mL to about 48 mg/mL. In one embodiment, the one or more active ingredients, for example, AMD3100 or similar stem cell mobilizer, can be in a concentration of about 16 mg/mL to about 48 mg/mL. In one embodiment, the AMD3100 or similar stem cell mobilizer can be in a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL or about 48 mg/mL.

The one or more active ingredients, for example, Tacrolimus (FK506) or any FK506 derivative or analog, can be in a concentration of about 0.05 mg/mL to about 2 mg/mL. In one embodiment, the one or more active ingredients, for example, Tacrolimus (FK506) or any FK506 derivative or analog, can be in a concentration of about 0.3 mg/mL to about 1.6 mg/mL. In one embodiment, the Tacrolimus (FK506) can be in a concentration of about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, or about 2.0 mg/mL.

The one or more solubilizing agent can comprise any suitable solubilizing agent. In one embodiment, the one or more solubilizing agents can comprise (without limitation), 1-N-methly-2-pyrrolidone (NMP), propylene glycol, dimethylsulfoxide (DMSO), N,N-dimethylformamide (DMF), polyethylene glycol, tetrahydrofurfuryl alcohol, polyethyleneglycol ether, and/or N,N-dimethylacetamide. In one embodiment, the solubilizing agent is 1-N-methly-2-pyrrolidone (NMP). The one or more solubilizing agents can be in a concentration of about 200 mg/mL to about 800 mg/mL or about 200 mg/mL to about 450 mg/mL. In one embodiment, the concentration of the solubilizing agent, for example, the NMP, can be about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, 300 mg/mL, about 310 mg/mL, about 320 mg/mL, about 330 mg/mL, about 340 mg/mL, about 350 mg/mL, about 360 mg/mL, about 370 mg/mL, about 380 mg/mL, about 390 mg/mL, about 400 mg/mL, about 410 mg/mL, about 420 mg/mL, about 430 mg/mL, about 440 mg/mL, about 450 mg/mL, about 460 mg/mL, about 470 mg/mL, about 480 mg/mL, about 490 mg/mL, about 500 mg/mL, about 510 mg/mL, about 520 mg/mL, about 530 mg/mL, about 540 mg/mL, about 550 mg/mL, about 560 mg/mL, about 570 mg/mL, about 580 mg/mL, about 590 mg/mL, about 600 mg/mL, about 610 mg/mL, about 620 mg/mL, about 630 mg/mL, about 640 mg/mL, about 650 mg/mL, about 660 mg/mL, about 670 mg/mL, about 680 mg/mL, about 690 mg/mL, about 700 mg/mL, about 710 mg/mL, about 720 mg/mL, about 730 mg/mL, about 740 mg/mL, about 750 mg/mL, about 760 mg/mL, about 770 mg/mL, about 780 mg/mL, about 790 mg/mL, or about 800 mg/mL. In one embodiment, the NMP can serves as a solvent and penetration enhancer, for example to promote absorption of the one or more active ingredients. In one embodiment, one or more solvents or penetration enhancers, in addition to NMP, can be used.

The one or more emollients and/or solvents can comprise any suitable emollient and/or solvent. In one embodiment, the one or more emollients and/or solvents comprise glycerin, propylene glycol, ethylene glycol, and/or ethanol. In one embodiment, solvent is glycerin. The emollients and/or solvents can be in a concentration of about 130 mg/mL to about 350 mg/mL. In one embodiment, the concentration of the emollient and/or solvent, for example, glycerin, can be about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, about 300 mg/mL, about 310 mg/mL, about 320 mg/mL, about 330 mg/mL, about 340 mg/mL, or about 350 mg/mL.

The one or more solvents can also comprise dimethyl sulfoxide (DMSO) or dehydrated ethanol or anhydrous ethanol. The one or more solvents can be in a concentration of about 20 mg/mL to about 70 mg/mL. In one embodiment, the concentration of the solvent, for example, dehydrated or anhydrous ethanol, can be about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, or about 70 mg/mL.

The one or more salts can comprise any suitable salts and/or osmotic agents. In one embodiment, the one or more salts and/or osmotic agents can comprise sodium chloride (NaCL), acetate, phosphate or diphosphate, citrate, mesylate, nitrate, tartrate, or gluconate. The one or more salts and/or osmotic agents can be in a concentration of about 1 mg/mL to about 3 mg/mL. In one embodiment, the concentration of the salt and/or osmotic agent, for example, sodium chloride (NaCl), can be about 1 mg/mL, about 1.5 mg/mL, about 2 mg/mL, about 2.5 mg/mL, or about 3 mg/mL.

The one or more pH adjusters can comprise any suitable pH adjuster. In one embodiment, the one or more pH adjusters comprise hydrochloric acid (HCl) and/or sodium hydroxide (NaOH). The one or more pH adjusters, for example, hydrochloric acid (HCl) and/or sodium hydroxide (NaOH), can be in a concentration sufficient for appropriate pH adjustment. In one embodiment, the pH adjuster can be in a concentration of about 1N to about 8N. In one embodiment, the pH adjuster, for example, hydrochloric acid (HCl) and/or sodium hydroxide (NaOH), can be in a concentration of about 2N.

In one embodiment, the formulation can comprise water for injection (WFI). The WFI can be in a concentration appropriate for Q. S. In one embodiment, the WFI concentration can be about 5-15% or about 50-150 mg/mL.

In one embodiment, the formulation can comprise the following components, which may be referred to herein as "Formulation A" or "FORM. A".

TABLE 1

Formulation A

| Active Ingredient/Excipient | Concentration (mg/mL) |
|---|---|
| AMD3100 (Active Pharmaceutical Ingredient) | about 16-48 |
| FK506 (Active Pharmaceutical Ingredient) | about 0.05-2.0 |
| 1-N-Methly-2-Pyrrolidone (NMP) | about 200-800 |
| Glycerin | about 130-300 |
| Dehydrated Ethanol | about 20-70 |
| Sodium Chloride (NaCL) | about 1-3 |
| Water for Injection (WFI) | for sufficient quantity (Q.S.) |

TABLE 1-continued

Formulation A

| Active Ingredient/Excipient | Concentration (mg/mL) |
|---|---|
| Hydrochloric Acid (HCl) | for pH adjustment |
| Sodium Hydroxide (NaOH) | for pH adjustment |

The pharmaceutical formulations disclosed herein may comprise formulations having improved stability profiles. The formulations may be suitable for injection delivery, for example subcutaneous injection. In an embodiment, formulations of the present disclosure provided surprising and unexpected improvements in the stability of Tacrolimus (FK506) and/or AMD3100. In one embodiment, the formulation, for example, injection comprising allows the active ingredients, Tacrolimus (FK506), or FK506 derivative or analog, and AMD3100, or similar stem cell mobilizer, to be stable under 2-8° C. or −20° C. for at least 9 months. In one embodiment, the formulation, for example, injection allows the active ingredients, Tacrolimus (FK506) or FK506 derivative or analog and AMD3100, or similar stem cell mobilizer, to be stable at room temperature for at least 10 days.

In one embodiment, the formulations of the present disclosure can result in peak blood levels of Tacrolimus (FK506) or FK506 derivative or analog of between 4 to 25 ng/mL at about 1 to about 3 hours. In one embodiment, trough levels can be less than 5 ng/mL. In one embodiment, the active ingredients AMD3100 and Tacrolimus can reach peak levels at substantially the same time, for example, about 1 to 3 hours, which can result in a surprising and unexpected synergistic effect of the active ingredients, for example, in activation of circulating stem cells. Subcutaneous injection of the formulations of the present disclosure can result in the synergistic effect. In one embodiment, stem cells in peripheral blood can reach peak levels at about 2 to about 3 hours, and mobilized stem cells can be exposed to the relatively low-level Tacrolimus for relatively short times.

In one embodiment, inclusion of 1-N-Methly-2-Pyrrolidone (NMP) in the formulations and methods of the present disclosure may provide an unexpected and/or synergistic effect. For example, NMP in a therapeutically effective amount, for example about 200 mg/mL to about 800 mg/mL or about 200 mg/mL to about 450 mg/mL, in the formulations of the present disclosure may regulate, activate or have another effect on the Bone Morphogenetic Protein (BMP) pathway in a patient or subject in a manner that may result in an unexpected effect and/or synergistic effect. In one embodiment, the combination of NMP, Tacrolimus or a derivative or analog thereof, and/or AMD3100 or a similar stem cell mobilizer may provide an unexpected and/or synergistic effect in the treatment of various conditions or diseases, including those disclosed herein, for example, by regulating, activating or otherwise affecting the BMP pathway in a patient or subject.

The methods and formulations disclosed herein result in pharmaceutical formulations that are formulated for subcutaneous injection. In one embodiment, the pharmaceutical formulations comprising AMD3100, or similar stem cell mobilizer, and Tacrolimus (FK506), or FK506 derivative or analog, are for single dose subcutaneous injection. In one embodiment, the pharmaceutical formulations display improved stability. In an embodiment, the present disclosure further comprises methods for stabilizing disclosed pharmaceutical formulations.

In an embodiment, the formulations of the present disclosure may be utilized for treating one or more therapeutic indications. In one embodiment, formulations of the present disclosure can be used to treat various types of tissue injury, spinal cord injury, myocardial infarction, corneal injury, skin wounds, etc. In one embodiment, formulations of the present disclosure can be used to treat various diseases or disorders, for example, one or more of tissue injury, burn wounds and injuries, autoimmune diseases, inflammatory diseases, inflammatory bowel disease, ulcerative colitis, Crohn's disease, organ transplant (including liver, heart, lung, kidney or corneal transplant or a skin graft), corneal injuries, corneal diseases and disorders, corneal wounds, lacerations, tears, wounds, punctures or combinations thereof, injuries related to or resulting from diabetes, spinal cord injury, nerve injury and/or degeneration, full-thickness burns or soft tissue injuries, ulcers, diabetic ulcers, organ injuries due to ischemia, surgery/trauma, infection/inflammation, autoimmune including heart, lung, liver kidney, stomach, intestines, kidney, skin, brain, spinal cord, musculoskeletal and vascular system, post-surgical adhesions (for example, postsurgical intraabdominal adhesions), etc. In an embodiment, formulations of the present disclosure can be used to treat, or can be used as an immunomodulatory and/or regenerative therapy for, Acute Respiratory Distress Syndrome (ARDS). In an embodiment, formulations of the present disclosure can be used to treat, ameliorate or improve arthritis and/or joint damage.

In an embodiment, the present disclosure comprises methods for manufacturing pharmaceutical formulations. In one embodiment, methods for manufacturing pharmaceutical formulations, for example Formulation A, can comprise one or more of the following steps in order or not in order: (i) remove drug substances from 2-8 C°; (ii) equilibrate drug substances, for example, for a minimum of 30 minutes; (iii) dispense 3-5% batch size with WFI; (iv) add appropriate amounts of salt, for example, sodium chloride, to achieve 2 mg/mL solution; (v) mix solution until homogenous; (vi) add appropriate amounts of solvent, for example, glycerin to achieve 189.15 mg/mL solution; (vii) mix solution until homogenous; (viii) add half of the total amount of solubilizing agent, for example, NMP, of desired 412 mg/mL solution; (ix) mix solution until homogenous; (x) in a separate compounding vessel, add appropriate amounts of active ingredient, for example, AMD3100 or any similar stem cell mobilizer, to achieve 24 mg/mL; (xi) add appropriate amounts of solvent, for example, dehydrated ethanol, to achieve 39.45 mg/mL and cover vessel; (xii) allow to mix until active ingredient, for example, AMD3100, or similar stem cell mobilizer, is fully dissolved; (xiii) add dissolved active ingredient, for example, AMD3100, or similar stem cell mobilizer, solution to excipient solution and use WFI for rinses; (xiv) allow to mix until visually homogenous; (xv) measure pH/Adjust pH to target range of 5.5-6.0 using pH adjuster, for example, 2N HCl and/or 2N NaOH; (xvi) in a separate compounding vessel, add appropriate amounts of active ingredient, for example, FK506 or FK506 derivative or analog, to achieve desired concentration of 0.5 mg/mL; (xvii) add the remaining half of the total amount of solubilizing agent, for example, NMP, to achieve desired concentration of 412 mg/mL; (xviii) mix solution until active ingredient, for example, FK506 or FK506 derivative or analog, is visually dissolved; (xix) transfer active ingredient solution, for example, FK506 solution or FK506 derivative or analog, to compounding vessel containing the other active ingredient, for example AMD3100, or similar stem cell mobilizer; (xx) mix solution until visually homogenous; (xxi) measure pH/Adjust to target range of 5.5-6.0 using pH adjuster, for example minimum of 2N HCl and/or 2N NaOH; (xxii) Q.S. to target weight using WFI; (xxiii) mix final drug product; (xxiv) sterile filter using sterilizing filter, for example, polyvinylidene fluoride (PVDF) 0.22 µm sterilizing filter; (xxv) store finished drug product at −20° C.

In an embodiment, the pharmaceutical formulations of the present disclosure comprise administering to a subject in need thereof a pharmaceutical formulation, wherein the pharmaceutical formulation comprises at least two active ingredients, for example AMD3100, or similar stem cell mobilizer, and Tacrolimus, or FK506 derivative or analog, wherein the dosing regimen comprises administering a fixed dose subcutaneous injection on multiple days, for example, on day 1, day 2 or day 3 following diagnosis or identification of the condition or symptoms to be treated, and additional applications. In one embodiment, the dosing regimen for the pharmaceutical formulations of the present disclosure comprises administering at least two active ingredients, for example AMD3100, or similar stem cell mobilizer, and Tacrolimus or FK506 derivative or analog, subcutaneously every other day. In one embodiment, the dosing regimen for the pharmaceutical formulations of the present disclosure comprises administering AMD3100, or similar stem cell mobilizer, and Tacrolimus, or FK506 derivative or analog, subcutaneously every other day for at least six (6) days or until the wound, injury or disease being treated has healed or improved.

Also provided herein are kits comprising at least one dosage form of the disclosure, for example a single dose subcutaneous injection, and instructions for administering the at least one dosage form to a subject. The kit can also comprise packaging or a container housing the at least one dosage form of the disclosure, and can also comprise instructions on storage, administration, dosing or the like and/or an insert regarding the active ingredient. The kit can also comprise instructions for monitoring circulating levels of the active ingredient (or metabolites thereof) once administered, and optionally, materials for performing such assays including, e.g., reagents, well plates, containers, markers or labels, and the like. Other suitable components to include in kits of the disclosure will be readily apparent to one of skill in the art, taking into consideration the desired indication, dosing regimen, storage conditions and route of administration.

In some embodiments, the formulations of the disclosure are stable when subject to predetermined conditions for predetermined times. For example, pharmaceutical formulations of the disclosure can be stored at various predetermined temperatures and relative humidities, for defined or predetermined time periods, for example in an open or closed container. In some embodiments, formulations of the disclosure are stable upon storage at about 2, 3, 4, 5, 6, 7 or 8 degrees Celsius and about [0%, 5%, 10%, 15%, 20%, 25%, 30%, 35%, 40%, 45%, 50%, 55%, 60%, 65%, 70%, 75%, 80%, 85%, 90%, 95% or 100% relative humidity] for a period of at least about 0.5, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 20, 25, 30, 35, 40, 45, 48, 50, 51, 52, 53, 55 or 60 hours, 1 week, 2 weeks, 3 weeks or 4 week; 1 month, 2 months, 3 months, 4 months, 5 months, 6 months, 7 months, 8 months, or 9 months. In one embodiment, the formulations of the present disclosure are stable at room temperature for at least 0.5, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 20, 25, 30, 35, 40, 45, 48, 50, 51, 52, 53, 55 or 60 hours, 1 day, 2 days, 3 days, 4 days, 5 days, 6 days, 7 days, 8 days, 9 days or 10 days. In some embodiments, formulations of the present disclosure are stable at about −20 degrees Celsius for long term, for example, up to two (2) years or longer.

Although exemplary amounts or ranges for the active ingredients and excipients are given, pharmaceutical formulations of the disclosure can comprise any amount of these components suitable for the purposes of obtaining the desirable pharmacologic and stability properties as described herein.

The pharmaceutical formulations of the disclosure can be formulated for administration as a fixed dose combination drug containing two or more APIs, for example AMD3100, or similar stem cell mobilizer, and Tacrolimus (FK506) or FK506 derivative or analog. In one embodiment, formulations of the present disclosure can be formulated as a fixed, single dose subcutaneous injection for continuous or periodic discontinuous administration. For continuous administration, a kit can include the pharmaceutical formulations of the disclosure in individual unit dosage forms (e.g., in separate single-use tubes or the like), and optionally instructions for administering the individual unit dosage forms, for example, more than once daily, daily, weekly, or monthly, for a predetermined length of time or as prescribed.

Suitable packages or containers are known in the art for holding and dispensing pharmaceutical formulations for subcutaneous injection. In one embodiment, the package comprises indicators for each administration period. In another embodiment, the package comprises labeled tubes for injection. The kits of the disclosure can also comprise a means for containing any type of packaging that houses the unit dosage forms, for example patches, injection tubes, which can (for example) be held in close confinement for commercial sale such as, e.g., injection or blow-molded plastic containers into which sealed pouches are retained. In one embodiment, prefilled syringes can be used for administration of the formulations of the present disclosure.

The therapeutically effective amount of a pharmaceutical formulation of the disclosure provided to a subject will vary depending upon the purpose of the administration, the state of the patient, level of pain and/or itch, and the like. As used herein, "subject" includes any human or non-human animal in need of treatment with the pharmaceutical formulations of the disclosure. In one embodiment, a subject is any human in need of treatment with the formulations of the disclosure (sometimes referred to herein as a "patient"). A therapeutically effective amount of the active ingredients in the pharmaceutical formulations of the disclosure can be determined by an ordinarily skilled physician, veterinarian or other medical professional, taking into account certain variables, including the specific condition and the size, age, weight, gender, disease penetration, previous treatment and response pattern of the subject.

The following examples are given to illustrate exemplary embodiments of the present disclosure. It should be understood, however, that the present disclosure is not to be limited to the specific conditions or details described in these examples.

EXAMPLES

While the present disclosure has been discussed in terms of certain embodiments, it should be appreciated that the present disclosure is not so limited. The embodiments are explained herein by way of example, and there are numerous modifications, variations and other embodiments that can be employed that would still be within the scope of the present disclosure.

Example 1—Pharmacokinetics and Pharmacodynamics of Formulation A and Toxicity in Rats and Pigs PK/PD studies: SD rats (200-300 gram) were given 0.744 ml/kg Formulation A (AMD3100 of 17.856 mg/kg, FK506 of 0.372 mg/kg) or mini pigs (9-10 kg) were given 0.132 ml/kg Formulation A (AMD3100 of 3.168 mg/kg, FK506 of 0.066 mg/kg) as a subcutaneously injection. The dose was given equivalent to 12 times in human (0.01 mg/kg: AMD3100 of 0.24 mg/kg, FK506 of 0.005 mg/kg).

Blood samples for the determination of plasma AMD3100 and FK506 concentrations were collected immediately before dosing and at 1, 2, 3, 6 12 and 24 hours after administration. Plasma samples were analyzed for AMD3100 and FK506 in accordance with the Food and Drug Administration guidelines on validating bioanalytical methods. All samples were frozen and stored at −70° C. on receipt. The samples were analyzed by liquid chromatography with tandem mass spectral detection.

Figure 1B:
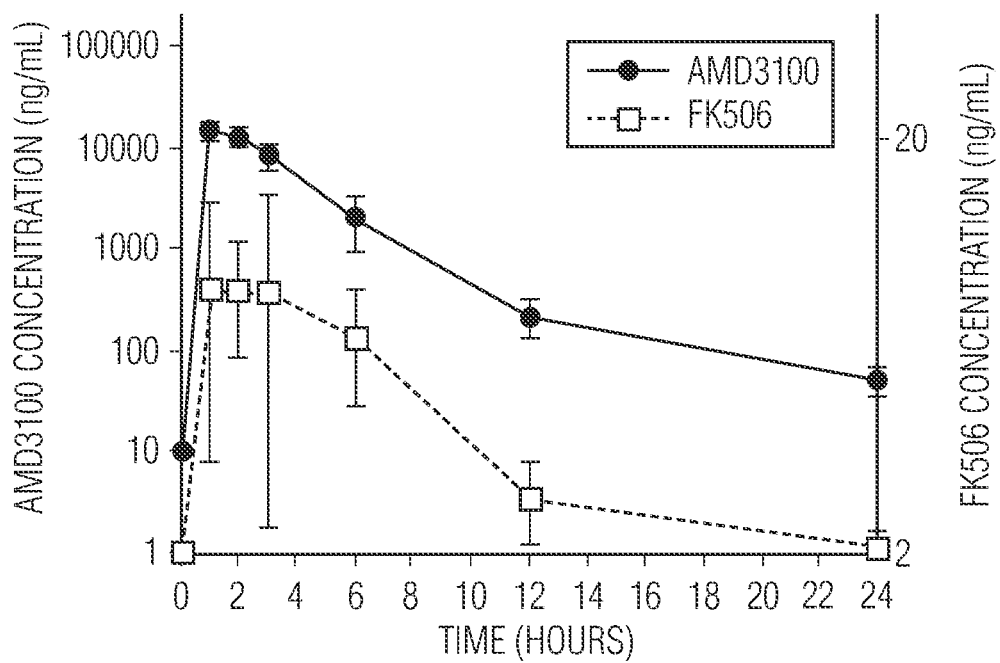
FIG. 1B shows mean AMD3100 and FK506 plasma concentrations over time on semilogarithmic scales in rats, according to an exemplary embodiment of the present disclosure.

Results: FIGS. 1A and 1B show mean AMD3100 and FK506 blood plasma concentrations over time on linear (FIG. 1A) and semilogarithmic (FIG. 1B) scales in rats as a function of time following Formulation A subcutaneous injection in SD rate (n=12). AMD3100 and FK506 were absorbed rapidly after s.c. administration with no observable lag time, with peak plasma concentrations of both APIs occurring at 1 hour after administration in rats and remained at high levels at 3 hours. The pharmacokinetics and pharmacodynamics were paralleled between AMD3100 and FK506. Both AMD3100 and FK506 were cleared within 12 hours.

Figure 2A:
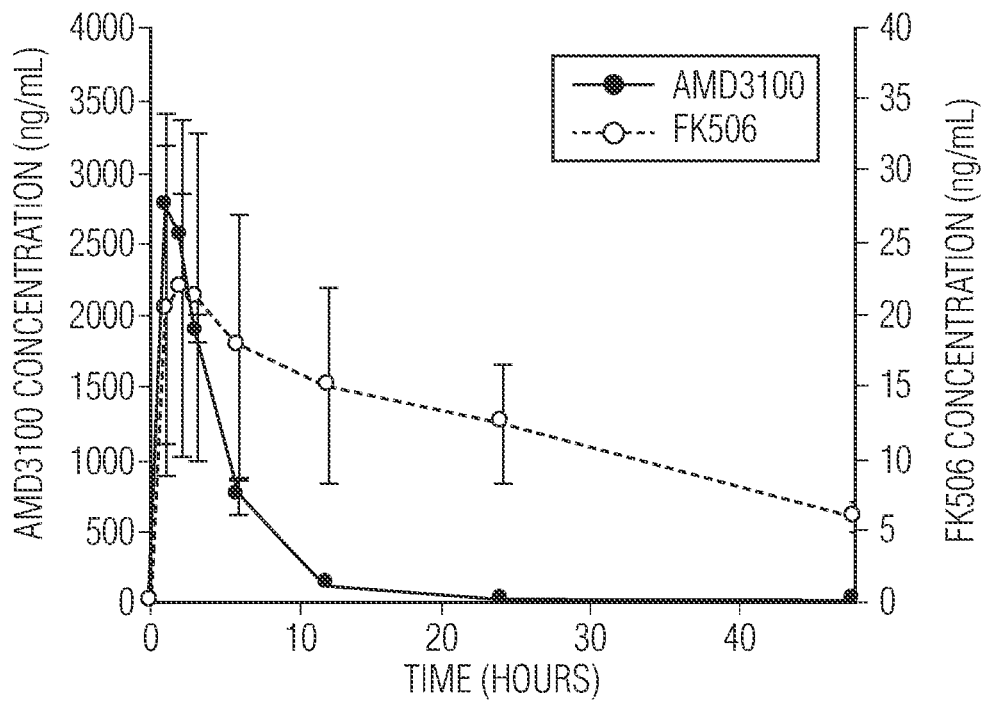
FIG. 2A shows mean AMD3100 and FK506 blood concentrations over time on linear scales in mini pigs, according to an exemplary embodiment of the present disclosure.
Figure 2B:
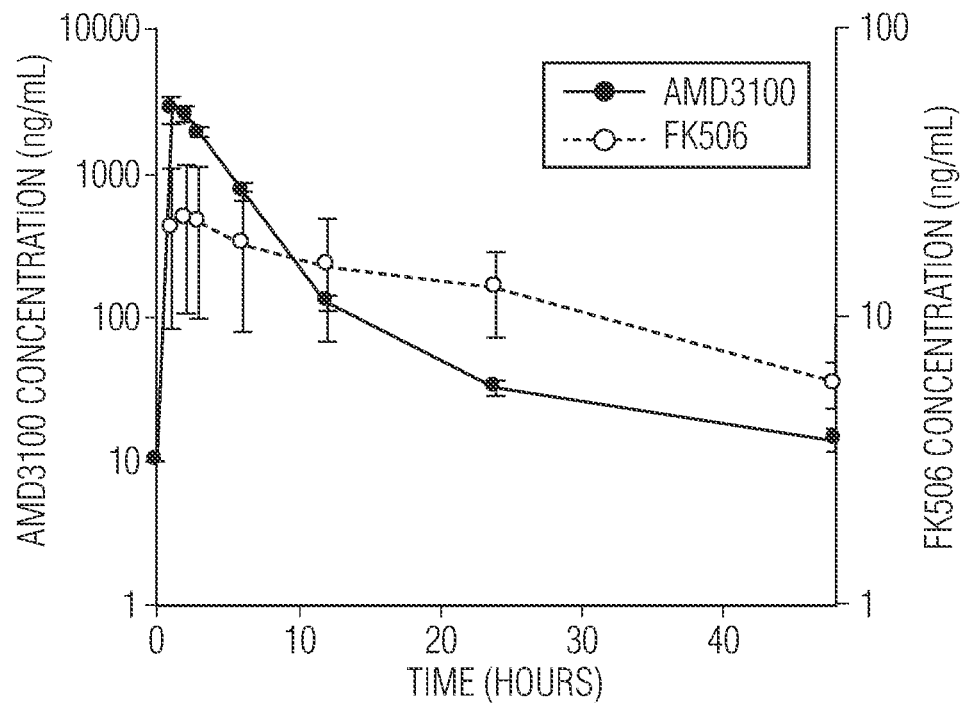
FIG. 2B shows mean AMD3100 and FK506 blood concentrations over time on semilogarithmic scales in mini pigs, according to an exemplary embodiment of the present disclosure.

FIGS. 2A and 2B show mean AMD3100 and FK506 blood concentrations over time on linear (FIG. 2A) and semilogarithmic (FIG. 2B) scales in mini pigs as a function of time following Formulation A subcutaneous injection (n=6). Both APIs reached peak levels at 1-2 hour after administration and remained at high levels at 3 hours. Both AMD3100 and FK506 were cleared rapidly after 12 hours.

Toxicity studies: A GLP study examined toxic effect of Formulation A in rats and mini pigs. Animals received dose equivalent to 12 times in human and repeat dosing at day 2, 4, 6, 8 and 10. No liver (AST. ALT, bilirubin, albumin) or kidney (creatinin and BUN) injury was found at treated concentration. Splenic enlargement, which is a common side effect of AMD3100, was not observed in both rats and mini pigs with Formulation A administration. Other organ systems were normal in animals received Formulation A every day for 10 days.

Example 2—Formulation A Appears to be Superior to Two Drugs Injected Separately for the Treatment of Inflammatory Bowel Disease (IBD) in Mice IL-10 knock out mice spontaneously develop a chronic inflammatory bowel disease (IBD). AMD3100 plus low-dose FK506 treatment can decrease colonic inflammation in the IL-10-deficient murine model of IBD (6). To determine if Formulation A is superior to AMD3100 plus low-dose FK506, the efficacy of Formulation A in IL-10-deficient mice was tested.

Methods: 5-month old IL-10-deficient mice (male and female) with the sign of IBD were used for this study and clinical progress of IBD was monitored. Disease activity index (DAI) was measured before and after drug treatment. Based on DAI, animals were divided into three treatment groups: 1) Saline control; 2) AMD3100 (2.4 mg/kg) plus FK506 (0.05 mg/kg); and 3) Formulation A.

Figure 3:
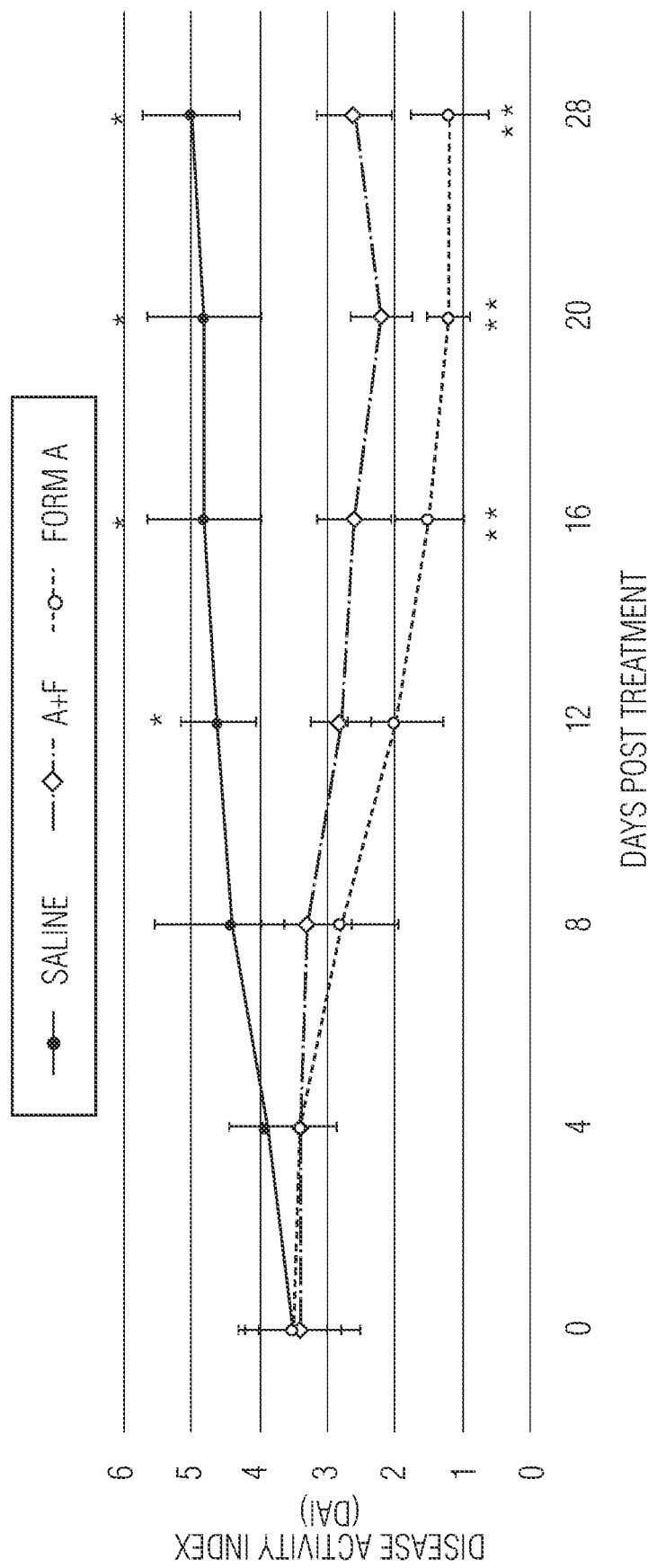
FIG. 3 shows Disease Activity Index (DAI) over time (days post treatment) for administration of AMD3100 plus FK506 or a formulation of the present disclosure, according to an exemplary embodiment of the present disclosure.

DAI was calculated by: weight loss (0 point=none, 1 point=1-5% weight loss, 2 points=5-10% weight loss, 3 points=10-15% weight loss and 4 points—more than 15% weight loss), stool consistency/diarrhea (0 points=normal, 2 points=loose stools, but still formed, 3 points=very soft, 4 points=watery diarrhea), bleeding (0 points=no bleeding, 2 points=slight bleeding, 3 points=blood trace in stool visible, 4 points, gross bleeding {by ColoScreen occult blood test (Helena Laboratories, Beaumont, TX)}). The sum of weight loss, diarrhea, and bleeding resulting in the total DAI score ranging from 0 (unaffected) to 12 (severe colitis). FIG. 3 shows administration of AMD3100 plus low-dose FK506 or Formulation A resulted in a significant improvement of the disease activity index in IL-10 knock out mice (*$p<0.01$ saline control vs. A+F or Formulation A group; **$p<0.05$ A+F vs. Formulation A).

Formulation A was diluted in saline (100×) before injection, and 10 ul/gram of diluted Formulation A (AMD3100 2.4 mg/kg, FK506 0.05 mg/kg) was injected subcutaneously every other day for 28 days. AMD3100 (2.4 mg/kg) and FK506 (0.05 mg/kg) were also diluted in saline before injection and each drug was injected separately. The same amount of saline was given in control animals.

Results: Administration of AMD3100 plus FK506 or Formulation A resulted in an improvement of the disease activity index in IL-10 knock out mice. DAI was gradually increased in a time-dependent fashion in animals treated with saline, but significantly decreased on day 12 and remained at lower levels in animals receiving AMD3100 plus low-dose FK506 (see FIG. 3). Surprisingly and unexpectedly, animals receiving Formulation A exhibited the lowest DAI after 16 days treatment. DAI was significantly lower in animals treated with Formulation A compared to AMD3100 plus FK506 group on day 16, 20 and 28. These results suggest that the fixed dose combination drug Formulation A may be superior to two drugs injected separately for the treatment of IBD.

Figure 4A:
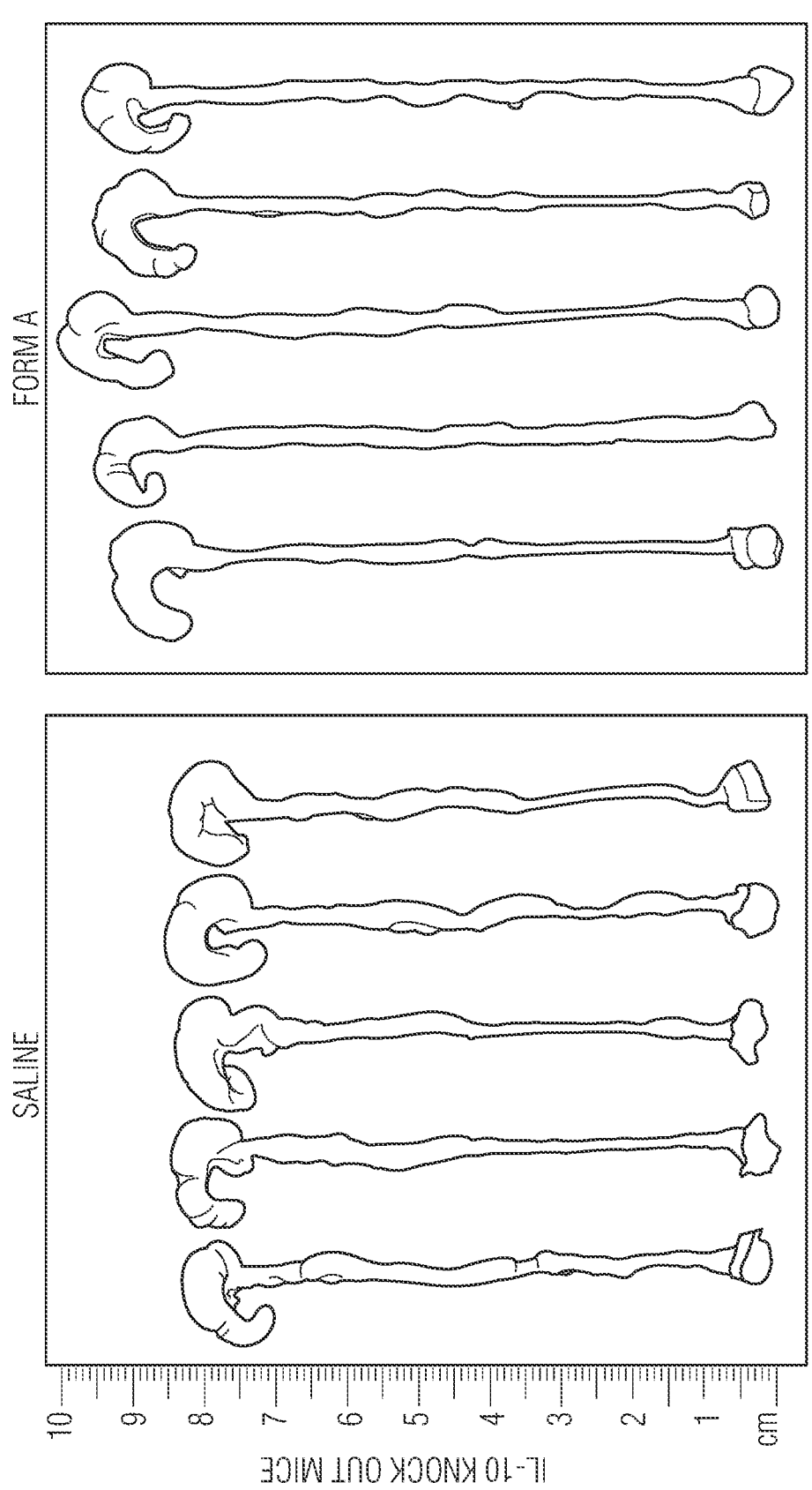
FIG. 4A shows pictures of colon length with treatment of a formulation of the present disclosure, according to an exemplary embodiment of the present disclosure
Figure 4B:
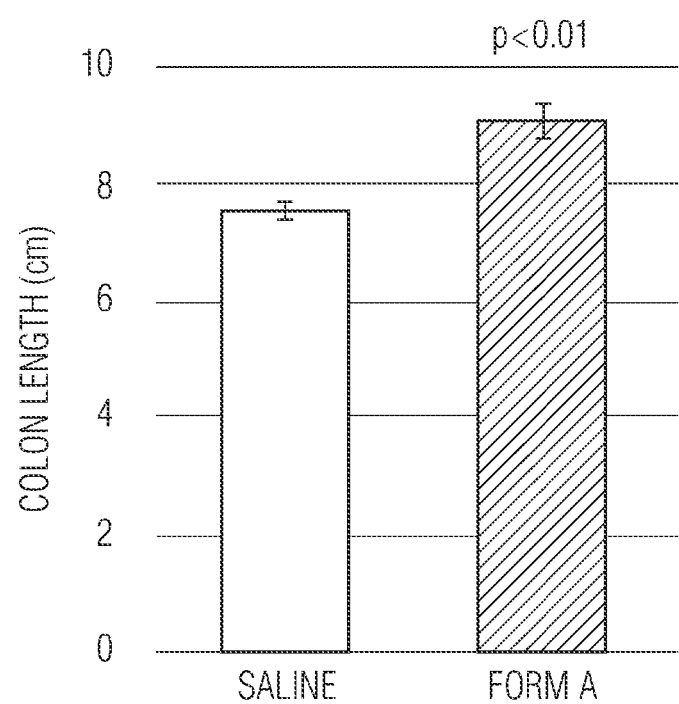
FIG. 4B shows quantitative data of colon length with treatment of a formulation of the present disclosure, according to an exemplary embodiment of the present disclosure.

Shortening of colon length in IBD mice is one of the biological markers in the assessment of colonic inflammation. FIGS. 4A and 4B show that Formulation A treatment can block colon shortening in 5 months old IL-10 knock out mice. FIG. 4A shows photos of the colons and FIG. 4B shows quantitative data of colon length. FIGS. 4A and 4B demonstrate that IL-10 knock out mice developed IBD and exhibited significant colon shortening compared to aged matched wild type mice, an effective which was unexpectedly eliminated by Formulation A treatment.

Summary: Formulation A (a fixed dose combination drug containing two APIs AMD3100 and FK506) may be superior to two drugs given separately for treatment of IBD. The advantage of Formulation A over two drugs is related to the novel formulation, drug absorption and pharmacokinetics and pharmacodynamics of Formulation A, as disclosed in the present disclosure.

Example 3: Formulation A Accelerated Wound Healing after Full-Thickness Skin Excision in Pigs Surgical excisional wounds: Female Yorkshire pigs 4-6 months in age and weigh 40-50 kg at arrival were acclimated for approximately 1-2 weeks prior to the experimental procedures. To create wounds, the pigs were sedated with telazol and xylazine combination 1.1-2.2 mg/kg dosage i.m. for induction and then intubated and maintained with sevoflurane or isoflurane 1-4% continuous inhalation. Six full-thickness wounds were generated by 4-cm diameter circular excisions on the shaved back of a pig (see FIG. 5A). Each wound site was photographed digitally at the indicated time intervals, and wound areas were calculated using Adobe Photoshop software. Changes in wound areas over time were expressed as the percentage of the initial wound areas.

Treatment: Wounded pigs were divided randomly into two experimental groups and received subcutaneous injections of saline or Formulation A (0.04 ml/kg) immediately after wounding until complete healing. All wound evaluations were double blinded.

Figure 5A:
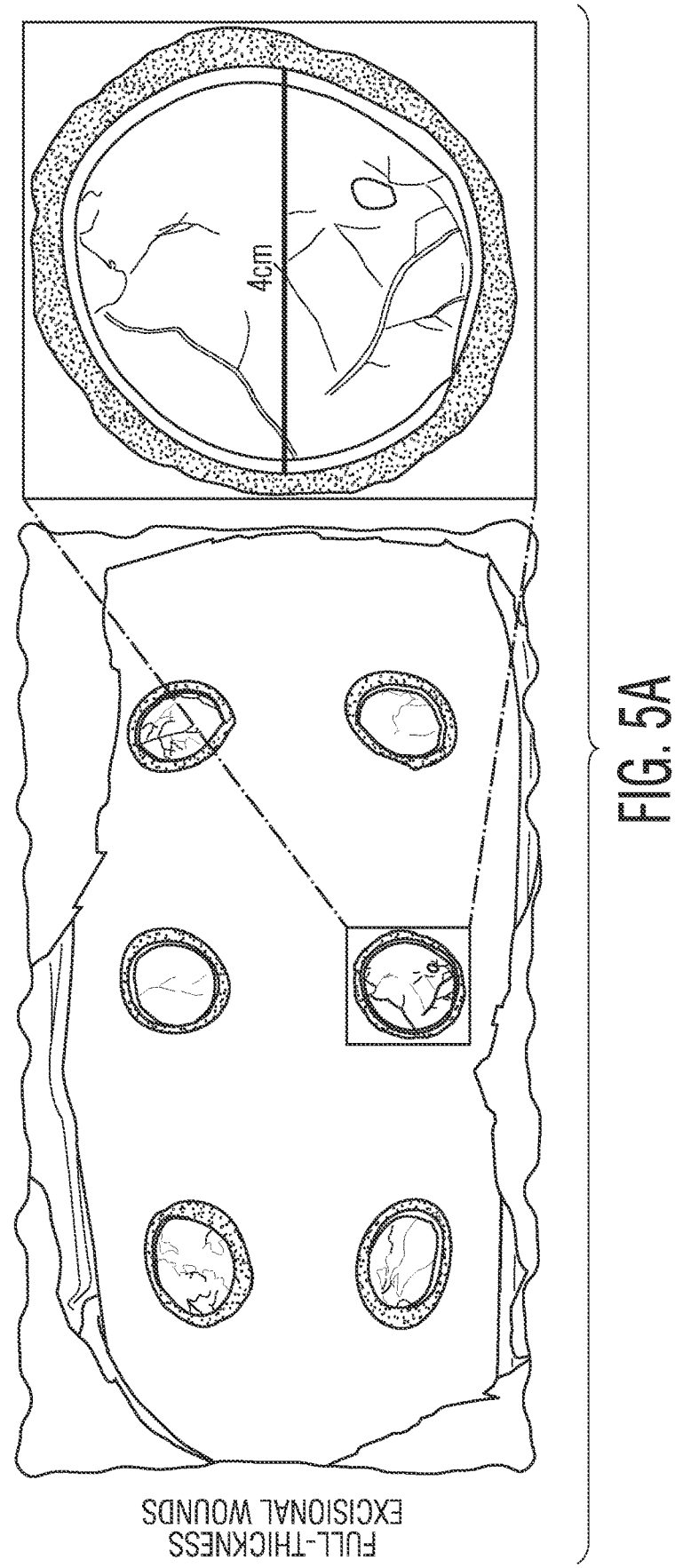
FIG. 5A shows a pig model on day 0 treated with a formulation of the present disclosure, according to an exemplary embodiment of the present disclosure.
Figure 5B:
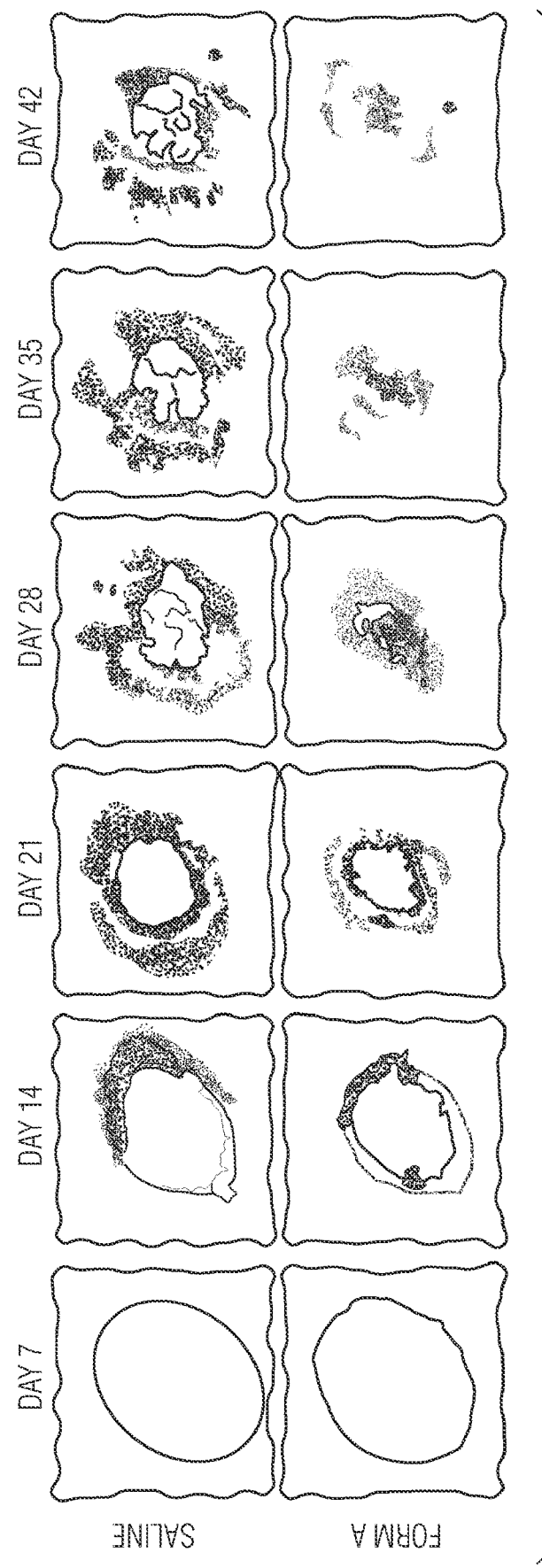
FIG. 5B shows macroscopic analysis of skin wound healing in a pig model treated with a formulation of the present disclosure, according to an exemplary embodiment of the present disclosure.
Figure 5C:
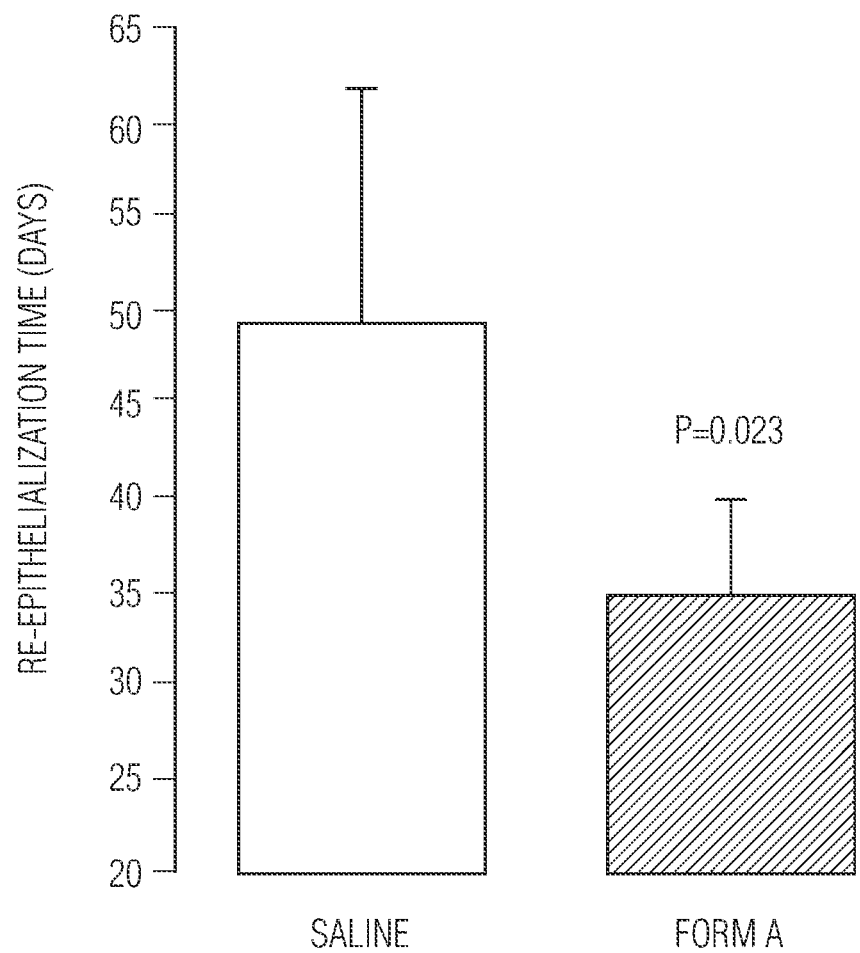
FIG. 5C shows reepithelization time for skin wound healing in a pig model treated with a formulation of the present disclosure, according to an exemplary embodiment of the present disclosure.

Results: FIGS. 5A, 5B and 5) show accelerated wound healing in pigs treated with Formulation A. FIG. 5A shows the pig model on day 0 with six (6) circular excisional wounds created on the model. FIG. 5B shows macroscopic analysis of skin wound healing in the pig model. FIG. 5(C) shows reepithelization time (n=3). Wounds reached complete closure on day 49 after surgery in pigs (n=3) treated with saline. Three pigs treated with Formulation A exhibited significantly faster healing compared with the saline control group as wounds reached complete closure at day 35 (see FIGS. 5B and 5C). In summary, Formulation A treatment may accelerate wound healing in preclinical large animal models.

Figure 6A:
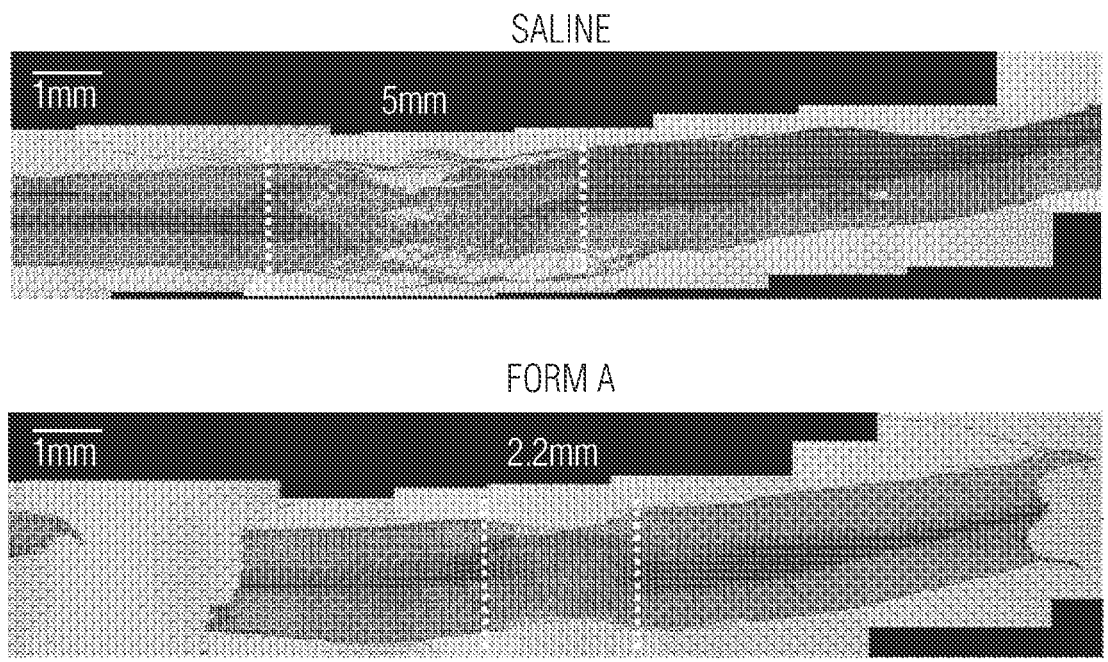
FIG. 6A shows histology of injured spinal cord at 1 month, according to an exemplary embodiment of the present disclosure.
Figure 6B:
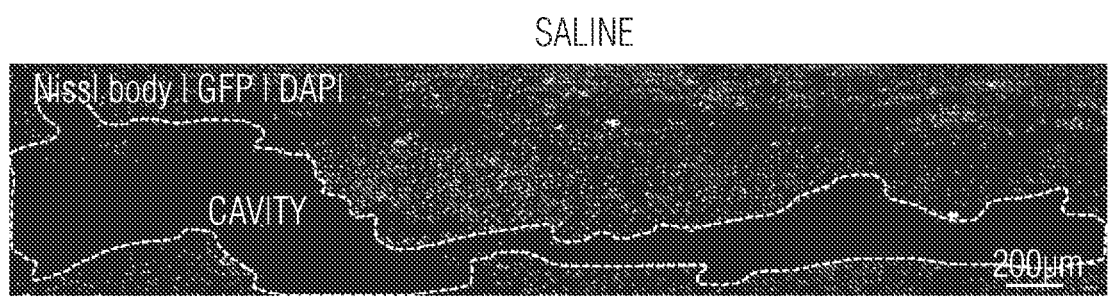
FIG. 6B shows bone marrow-derived GFP cells after SCI in rats after treatment with a formulation of the present disclosure, according to an exemplary embodiment of the present disclosure.
Figure 6B:
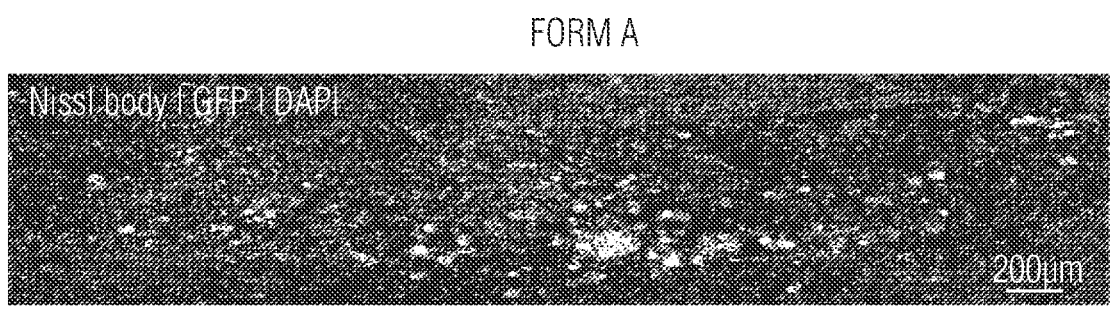
Figure 6C:
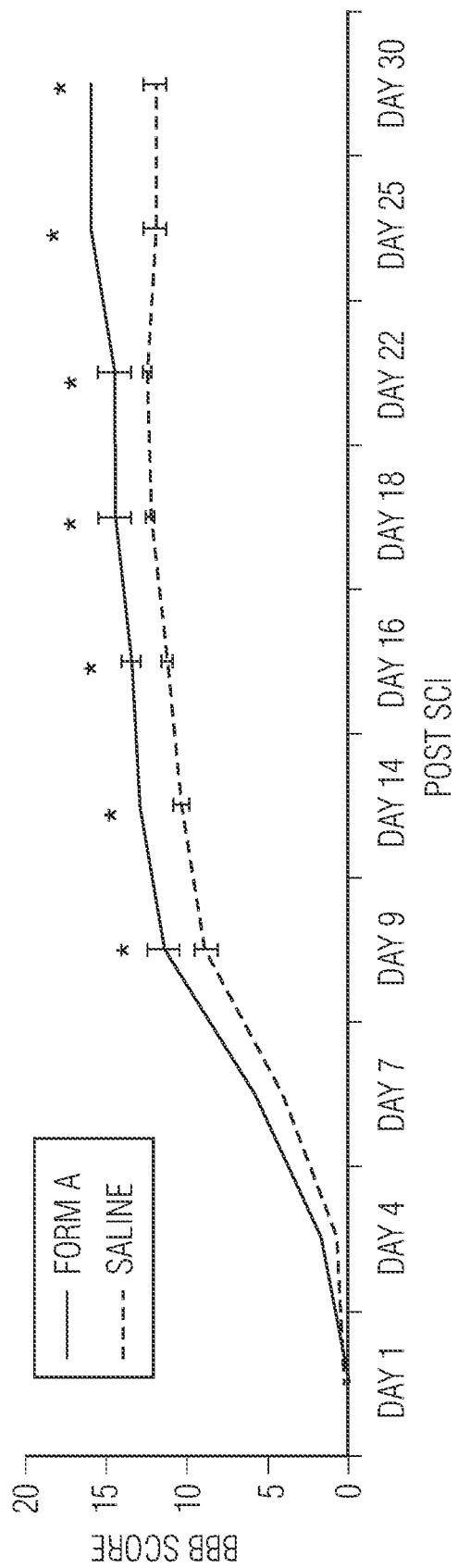
FIG. 6C shows BBB Score (Basso, Beattie and Bresnahan Score) over time for acute spinal injury (SCI) in rats after treatment with a formulation of the present disclosure, according to an exemplary embodiment of the present disclosure.

Example 4: Formulation A Improves Recovery after Acute Spinal Cord Injury (SCI) in Rats Summary: FIGS. 6A, 6B and 6C show that Formulation A improves functional recovery after acute spinal cord injury (SCI). Spinal cord contusion injury model was created in bone marrow transplantation Lewis rats (GFP+Lewis into wild type Lewis). Injured animals were given saline (n=7) or Formulation A (n=8) subcutaneous injection at 24 hours following SCI and every other day for one (1) month. FIG. 6A shows histology of injured spinal cord at 1 month. FIG. 6B shows few bone marrow-derived GFP cells accompanied with a large cavity in the injury area of spinal cord in saline treated rats, while numerous bone marrow-derived GFP+ cells appeared in the injury area of spinal cord in rats treated with Formulation A and no cavity was identified. FIG. 6C shows BBB score against time post-SCI.

Contusive spinal cord injury model in rats: A contusive rat model of SCI with weight drops from a height of 12.5 mm was performed in 5 to 6 months old Lewis rats. To determine the role bone marrow-derived stem cells in SCI, bone marrow from green fluorescence protein (GFP) transgenic Lewis rats were transplanted to lethally irradiated wild-type Lewis recipients. Three months later, bone marrow transplanted rats were used for SCI. Anesthesia was induced and maintained in animals with isoflurane inhalation (2-4%). The laminectomy was performed at thoracic vertebra T8 to expose the dorsal surface of the spinal cord. Stabilization clamps served to immobilize the T5 and T12 vertebrae to support the column during impact. Then the spinal cord at T8 was placed directly under the vertical shaft of the mechanical impactor NYU device and the shaft (tip diameter, 1 mm) is slowly lowered until the tip touches the cord. Next, the impactor probe was withdrawn to the desired impact drop distance (12.5 mm). A pin suspending the impact shaft was released and allowed to descend by gravity to hit the cord. The impactor was then withdrawn, the animal was removed from the device, and the muscle layers and skin were closed with 4-0 absorbable sutures. Antibiotics (Gentamicin) was then given every day to the rat to prevent urinary system infection. Pain killer was also given. At 7-10 days, sutures are removed under anesthesia.

Treatment: Animals recovered from surgery and showed hindlimb paralyzation at 24 hours following surgery were randomly divided into two groups and received subcutaneous injection of saline or Formulation A (0.1 ml/kg) every other day for 28 days.

Measurement: Post-injury motor behavior was assessed via the Basso, Beattie and Bresnahan (BBB) locomotor scale method. The BBB was used to assess joint movement, hindlimb movements, stepping, limbs coordination, trunk position, paw placement, and tail position. The recovery after SCI in rats was scaled from 0 to 21.

Results: At the end of the study, the spinal cords of all animals were investigated with histology. Hematoxylin/eosin staining of longitudinal sections revealed extensive tissue damage caused by the contusion injury in rats treated with saline (see FIG. 6A). At the lesion center, most tissue was destroyed in all cases. Cavitation occurred, and to a large extent the remaining tissue contained non-neuronal scar, necrotic tissue and infiltration of inflammatory cells. In contrast, the injury area was smaller and exhibits much less vacuolation and cell death when treated with Formulation A every other day. Immunofluorescence staining showed that a few bone marrow-derived GFP+ cell appeared in the lesion area and a large cavity was formed the lesion center in saline treated rats. Numerous bone marrow-derived GFP positive cells presented in the lesion center in Formulation A treated rats. Interestingly, some of large GFP+ cells contained Nissle body (red color) which is a large granular body found in neurons (see FIG. 6B). These results suggest mobilized bone marrow stem cells may become neuron cells in spinal cord.

At day 1 post-operation, all animals scored less than 2 in the BBB locomotor function scale demonstrating a reasonable degree of reliability of the SCI rat model. Due to spontaneous recovery, time significantly affected motor function in all treatment groups (FIG. 6C), and a significant difference was found between the saline control and the treatment over time. Importantly, rats treated with Formulation A had significantly better motor function (BBB scores).

Formulation A treatment mobilized and recruited bone marrow stem cells into the injured spinal cord, these stem cells repaired/regenerated damaged spinal cord tissues and improved the locomotor function.

Figure 7A:
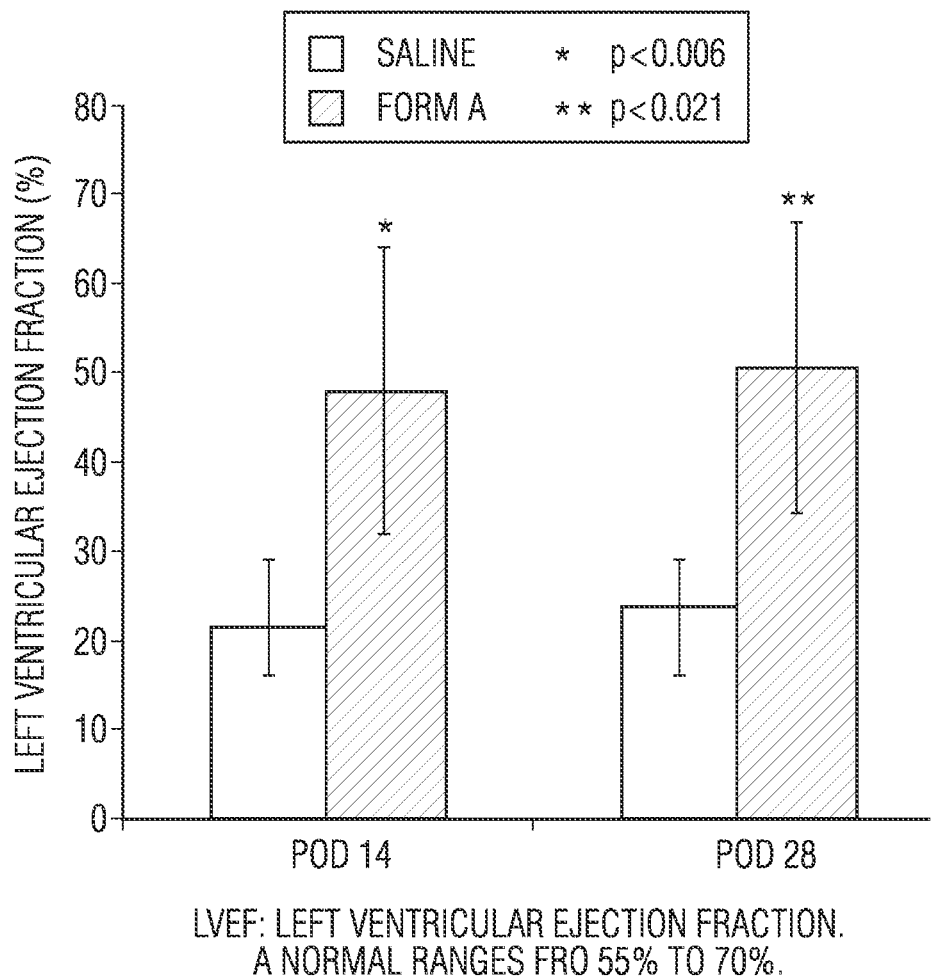
FIG. 7A shows left ventricular ejection fraction (LVEF) post operation following myocardial infarction in rats after treatment with a formulation of the present disclosure, according to an exemplary embodiment of the present disclosure.
Figure 7B:
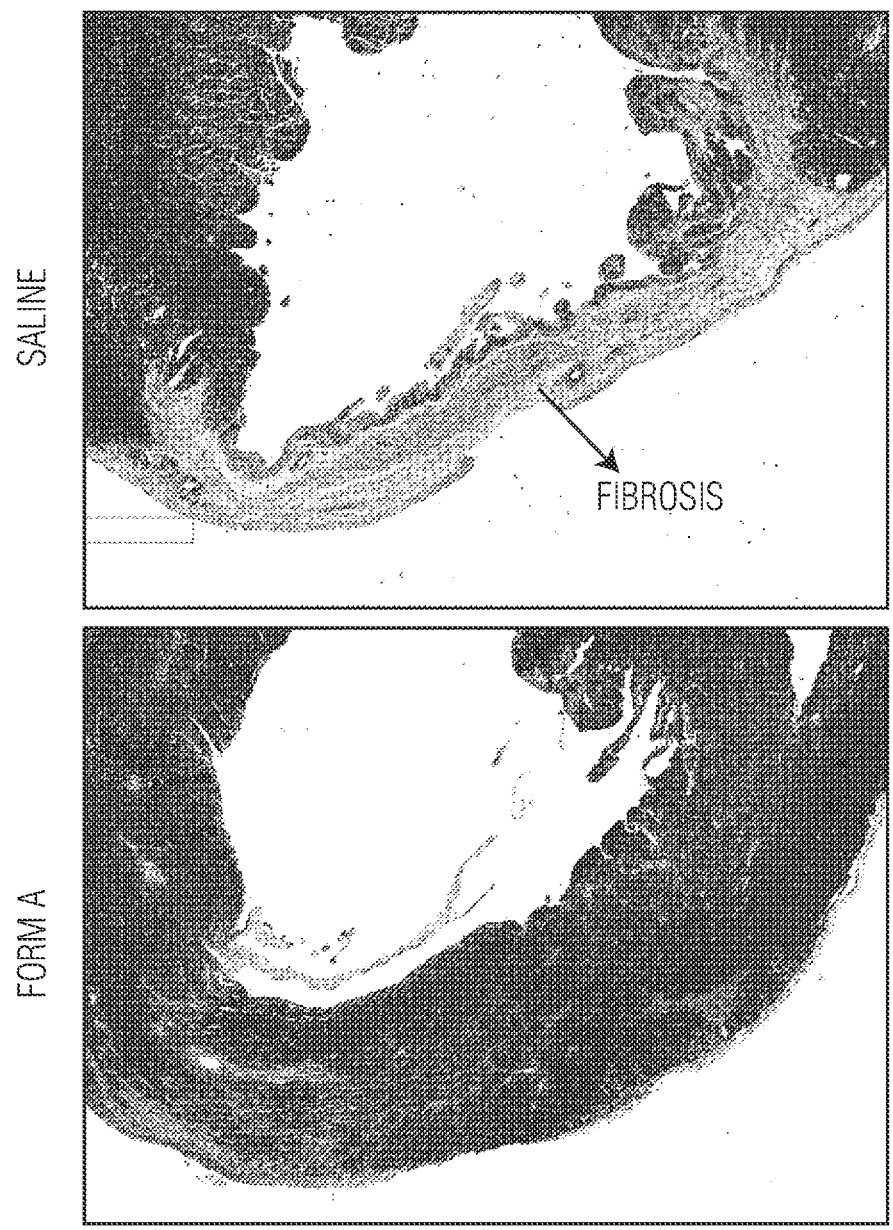
FIG. 7B shows Masson's trichome staining of showing scar formation post operation following myocardial infarction in rats after treatment with a formulation of the present disclosure, according to an exemplary embodiment of the present disclosure.

Example 5: Formulation A Treatment Improves Cardiac Function Following Myocardial Infarction in Rats Summary: FIGS. 7A and 7B shows Formulation A treatment improves cardiac function and ameliorates fibrosis following myocardial infarction in rats. FIG. 7A shows left ventricular ejection fraction (LVEF) at post operation day 14 and 28. FIG. 7B shows representative picture from 5 rats in each group and shows Masson's trichome staining showed scar formation in the left ventricular anterior wall of saline treated rats.

Induction of myocardial infarction in rats: Ten male Lewis rats ranging from 8 to 10 weeks in age and weighing 220-250 g were selected for inducing MI by LAD ligation. Anesthesia was induced and maintained in animals with an intra-peritoneal injection of ketamine and xylazine. After anesthesia, the animals were intubated and ventilated with a 16 gauge intravenous catheter and were placed in a supine position on a temperature control pad. The chest was opened by incision parallel to the ribs at the fifth intercostal space and the ribs were spread to expose the heart. The pericardium was opened with sharp forceps to access the heart. once the site of ligation of left anterior descending coronary artery (LAD) had been determined 5 mm away from the origin, a cotton ear bud was used to gently press on the artery a little below the site of ligation, immobilizing the heart and also making the artery prominent and easy to identify. Using a tapered atraumatic needle, a 6-0 silk ligature was passed underneath the LAD and tied with three knots. Visible blanching and cyanosis of the anterior wall of the left ventricle and swelling of the left atrium were indicative of successful ligation. The lungs were re-inflated, the thoracic wall was closed, and the rat was extubated when spontaneous breathing occurred.

Treatment: Animals recovered from surgery were randomly divided into two groups and received subcutaneous injection of saline or Formulation A (0.1 ml/kg) at 6 hour following surgery and every other day for 28 days.

Measurement: Echocardiography was performed at day and day 28 after induction myocardial infarction by ligation of the left anterior descending coronary artery in rats. Animals were sacrificed at 1-month post MI and cardiac histology was studied.

Results: Left ventricular ejection fraction (LVEF) is a one of major tests to determine cardiac function following MI and a range of LVEF between 50% to 70% is considered normal. Echocardiography performed on post operation day (POD) 14 and 28 showed the average of LVEF was about 20% in rats treated with saline following induction myocardial infarction by ligation of the left anterior descending coronary artery. In contrast, the levels of LVEF in Formulation A-treated rats were significantly higher (about 50%) on POD14 and remained at a higher level close to normal range on POD 28 (FIG. 7A). The histopathological examination of the heart of saline treated rats with MI at 1 month showed the left ventricular anterior wall was pale and thinner near the apex. Masson's trichrome staining showed scar formation in the left ventricular anterior wall. Interestingly, the left ventricular anterior wall remained thick showing uniform reddish color. Few fibrotic tissues staining with blue color appeared in cardiac smooth muscles (FIG. 7B). These results suggest that mobilization and recruitment of endogenous stem cells with Formulation A improves cardiac function following MI through ameliorating cardiac ischemic injury, promoting repair/regeneration and preventing scar formation.

Example 6: Formulation A Prevents Corneal Fibrosis Following Corneal Alkali-Burn Injury in Mice The corneal wound healing response, including the development of stromal opacity, is a process that often leads to scarring/fibrosis that occurs after injury, surgery or infection to the cornea. By reducing corneal transparency, corneal fibrosis can impair or completely diminish its function, leading to vision impairment and blindness. Mobilization and recruitment of bone marrow stem cells may promote corneal epithelial repair and ameliorate stromal fibrosis.

Figure 8A:
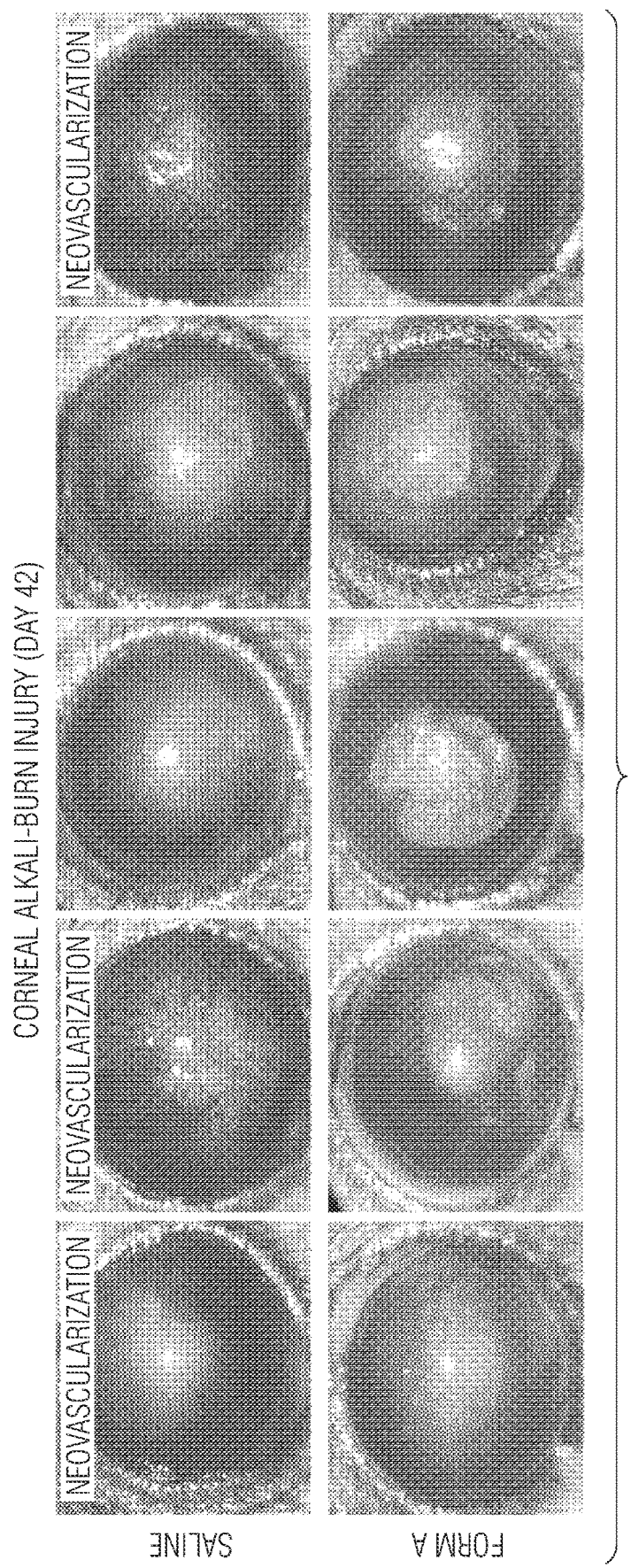
FIG. 8A shows pictures of eye corneas following eye burn in mice after treatment with a formulation of the present disclosure, according to an exemplary embodiment of the present disclosure.
Figure 8B:
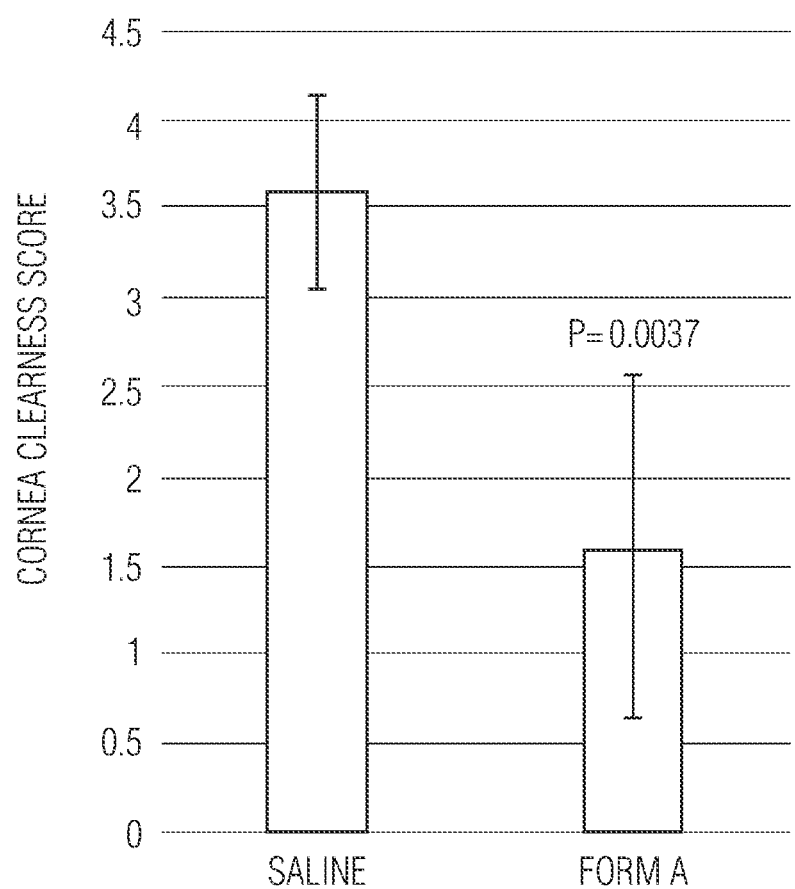
FIG. 8B shows mouse cornea clearness score following eye burn in mice after treatment with a formulation of the present disclosure, according to an exemplary embodiment of the present disclosure.

Summary: FIGS. 8A and 8B show Formulation A treatment prevents corneal scarring following eye burn in mice. One eye of C57/B6 mice was burned with 0.5N NaOH for 20 seconds. Animals were treated with saline or Formulation A subcutaneous injection every other day for 2 weeks following the eye burn. Corneal scar formation was measured at 42 days following injury. FIG. 8A shows pictures of the eye corneas (n=5) and FIG. 8(B) shows mouse cornea clearness score from 0 to 4 with 4 being the worst.

Methods: The corneal alkali-burn injury (0.5N NaOH for 20 seconds) was induced onto the cornea of one eye in C57/B6 mice. Formulation A was 10 times diluted in saline before injection. From the injury day, chemical burn-injured mice were treated with either saline or Formulation A (1 ml/kg) every other day. The ocular surface situation were assessed on day 1, day 3, day 7, day 14, day 21, day 30, day 37, and day 42. The corneas were obtained for histopathology evaluation. To determine if bone marrow-derived stem cells can repopulate the cornea, GFP transgenic bone marrow transplanted Lewis rats were studied.

Results: To determine if bone marrow-derived stem cells can repopulate the cornea, GFP transgenic bone marrow transplanted Lewis rats were studied. At 4 months post GFP bone marrow transplantation, GFP positive cells were identified in the stroma and epithelial layers of corneas indicating cornea contains a significant population of bone marrow-derived cells and bone marrow stem cells may play a role in the response of the cornea to injury.

Based on these findings, improvement of cornea healing following alkali-burn injury by mobilization and recruitment of bone marrow stem cells with Formulation A was tested. The corneas showed elevated reepithelization rate, less cornea opacity scores and no corneal neovascularization in the alkali burn model in the Formulation A treated group (see FIG. 8A). The HE staining and immunostaining showed less activated myofibroblasts, less intraocular inflammation and neovascularization in the experiment corneas.

In summary, this study may demonstrate that Formulation A accelerates healing and prevents fibrosis following corneal alkali-burn injury. Formulation A may be an effective therapy for corneal fibrosis in patients.

Example 7: Synergistic Effects of NMP with Formulation A

This study tested whether N-methyl-2-pyrollidone (NMP) increases the efficacy of AMD3100 and Tacrolimus combination (AF combination) treatment in a pig model for wound healing. Type 1 diabetic pigs were induced by streptozotocin (STZ), a glucosamine-nitrosourea compound derived from *Streptomyces achromogenes* that is used clinically as a chemotherapeutic agent in the treatment of pancreatic β cell carcinoma. STZ damages pancreatic β cells, resulting in hypoinsulinemia and hyperglycemia. Pigs were subsequently fed with a cholesterol-rich diet (2.0% cholesterol, 20% lard, commercially available through Envigo) for 20 weeks to induce atherosclerosis to mimic the clinical situation (ulcer patients with peripheral artery disease).

After 20 weeks, six full-thickness wounds were generated by 4 cm diameter circular excisions on the shaved back of a pig. Wounded pigs were divided randomly into four experimental groups as follows and received subcutaneous injections of saline or drugs immediately after wounding and every other day until complete healing: 1) control group treated with saline; 2) AF combo group treated with AMD3100 (0.5 mg/kg) plus low-dose FK506 (0.01 mg/kg); 3) NMP (8 mg/kg) and 4) AF combo plus NMP (8 mg/kg).

Figure 9A:
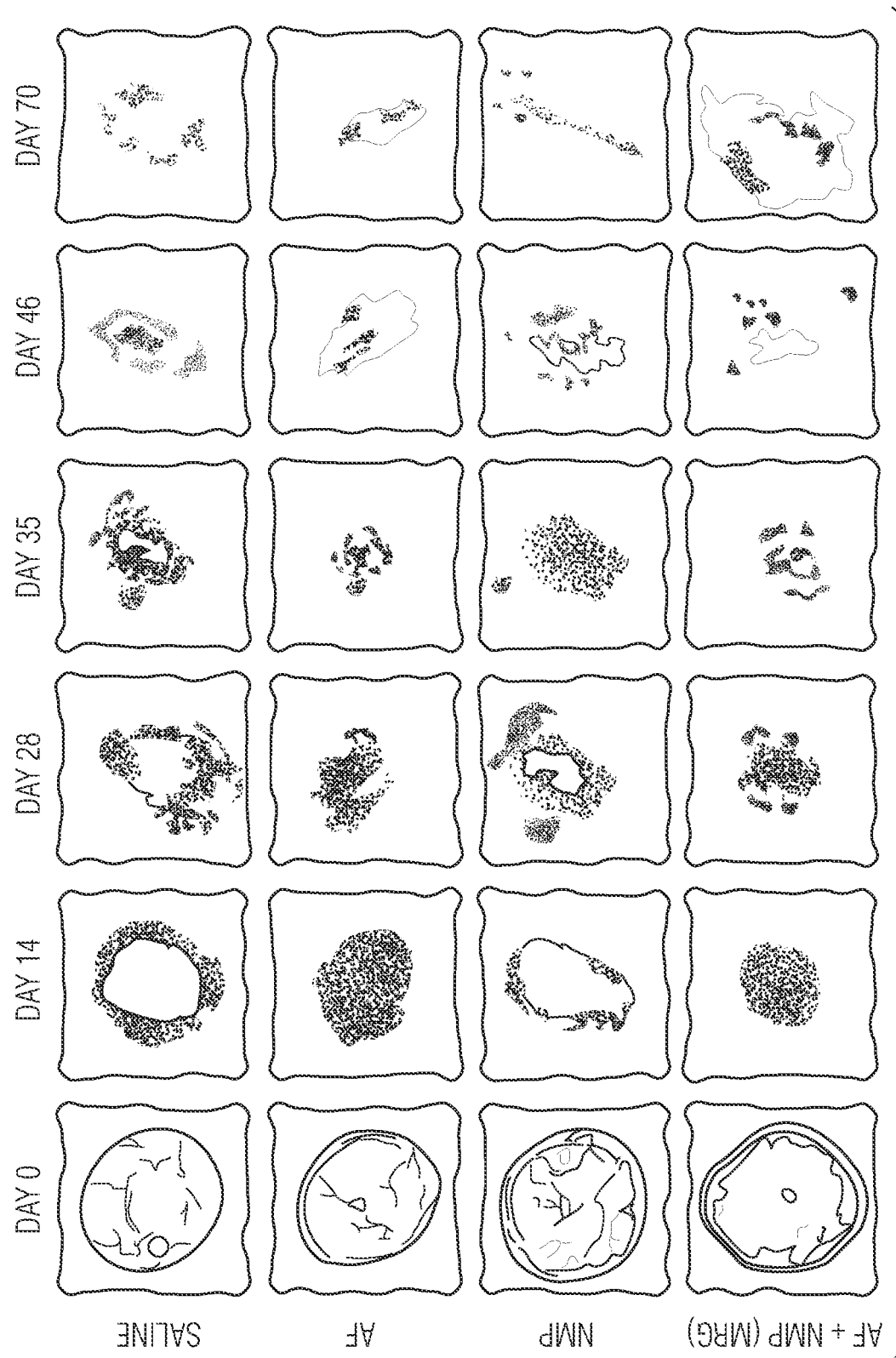
FIG. 9A shows macroscopic analysis of skin wound healing in pigs, according to an exemplary embodiment of the present disclosure.
Figure 9B:
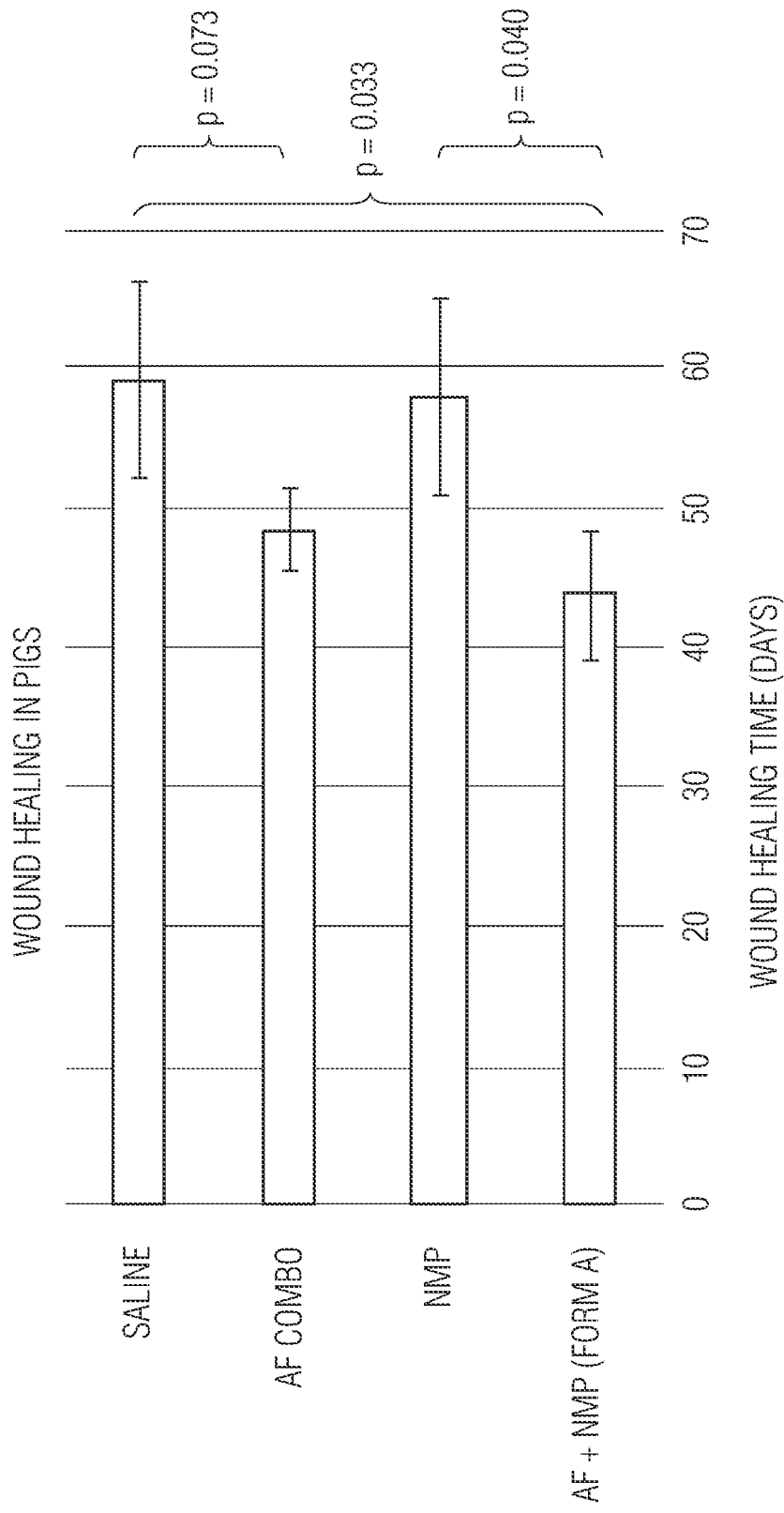
FIG. 9B shows wound healing time in type 1 pigs, according to an exemplary embodiment of the present disclosure.

FIGS. 9A and 9B demonstrate that NMP increases efficacy of AF combination in wound healing after full thickness excision in pigs. FIG. 9A shows macroscopic analysis of skin wound healing in pigs. Each wound site was photographed digitally at the indicated time intervals and wound areas were calculated using PhotoShop software. Representative pictures of 24 wounds from 3 pigs per group, 6 wounds per pig are shown in FIG. 9A. FIG. 9B shows the wound healing time. Wounds reached complete closure on day 59 after surgery in saline control group. The three animals treated with AF combination exhibited faster healing compared with the saline control group as wounds reached complete closure at day 48. The healing time was reduced to 43 days or by 27% in the group three pigs treated with AF combo plus NMP (FIG. 9B). The healing time was statistically different from saline control group (p=0.033) or the group treated with NMP (p=0.040). Digital images showed that treatment with AF plus NMP therapy had significant effects reducing the size of the skin defects as soon as day 14. These results suggest that NMP and AF combo unexpectedly exhibit a synergistically accelerated wound healing in pigs.

This study demonstrates that NMP may promote the efficacy of AF combo therapy in wound healing by inhibiting inflammation of the wounds via suppression of the mitogen-activated protein kinase signaling pathway and by enhancing bone morphogenetic protein (BMP) expression. NMP may exhibit anti-inflammatory functions, promote ankle fracture healing and bone tissue regeneration by inhibiting inflammation via suppression of the mitogen-activated protein kinase signaling pathway and enhancing BMP expression.

Example 8: Formulation A as an Immunomodulatory and Regenerative Therapy for Acute Respiratory Distress Syndrome Acute respiratory distress syndrome (ARDS) is a type of respiratory failure characterized by rapid onset of widespread inflammation in the lungs. ARDS can occur in those who are critically ill or who have significant injuries. It is often fatal, the risk increasing with age and severity of illness. Causes may include sepsis, pancreatitis, trauma, pneumonia, and aspiration. ARDS secondary to viral pneumonitis is one of the main causes of high mortality in patients with COVID-19. The mortality in COVID-19 patients with ARDS is about 39% (95% CI: 23-56%). There is no proven specific pharmacological treatment for patients with ARDS. Dexamethasone has been used in COVID-19 patients with ARDS, but is unproven and is associated with the increased risk of infectious complications.

Formulation A Reduced Mortality and Improved Survival in a Mouse Model of *Strep. pneumoniae* Induced Acute Respiratory Distress Syndrome (ARDS).

Figure 10A:
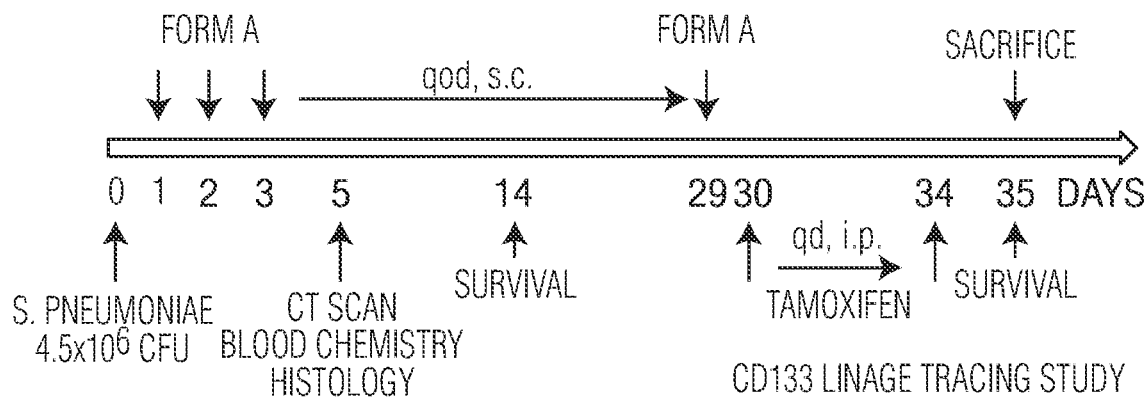
FIG. 10A shows experimental protocol for study of Formulation A in reducing mortality and improved survival in a mouse model of *Strep. pneumoniae* induced ARDS, according to an exemplary embodiment of the present disclosure.
Figure 10B:
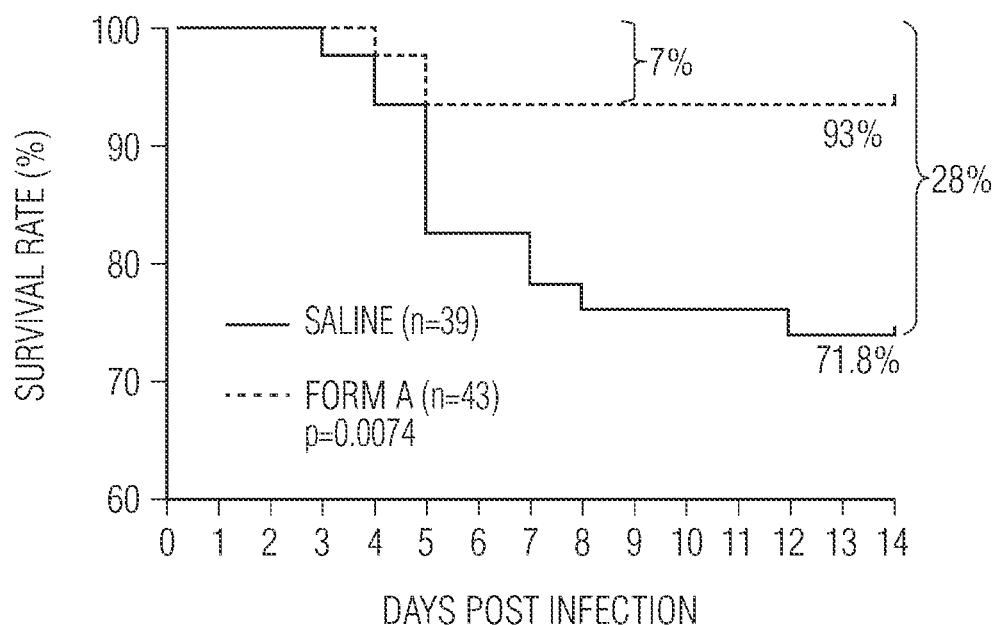
FIG. 10B shows the animal survival in a study of Formulation A in reducing mortality and improved survival in a mouse model of *Strep. pneumoniae* induced ARDS, according to an exemplary embodiment of the present disclosure.

FIGS. 10A and 10B demonstrates that Formulation A unexpectedly reduced mortality and improved survival in a mouse model of *Strep. pneumoniae* induced ARDS. FIG. 10A shows the experimental protocol and FIG. 10B shows the animal survival. To test whether Formulation A can ameliorate ARDS, C57/B6 mice were infected with *Streptococcus pneumoniae* in a standard model that induces ARDS through intratracheal instillation of $4.5 \times 10^6$ CFU *Streptococcus pneumoniae*. Infected animals were randomly divided into two groups and received placebo or Formulation A (0.1 ml/kg) treatment at 24 hours after infection and every other day until day 14 or day 28 (FIG. 1(A)). Animals exhibited body weight reductions (~10%) and respiratory distress before treatment, which indicated that all animals were successfully infected. Eleven out of 39 mice (28.2%) died in the placebo (saline) control group within 2 weeks after infection, which is consistent with the known mortality rate in this established model (6). The mortality rate was reduced to 7% (3 out of 43), or by 75%, in mice treated with Formulation A (FIG. 10B).

Formulation A Ameliorated Lobar Pneumococcal Pneumonia and Reduced Inflammation in the Lungs.

Figure 11A:
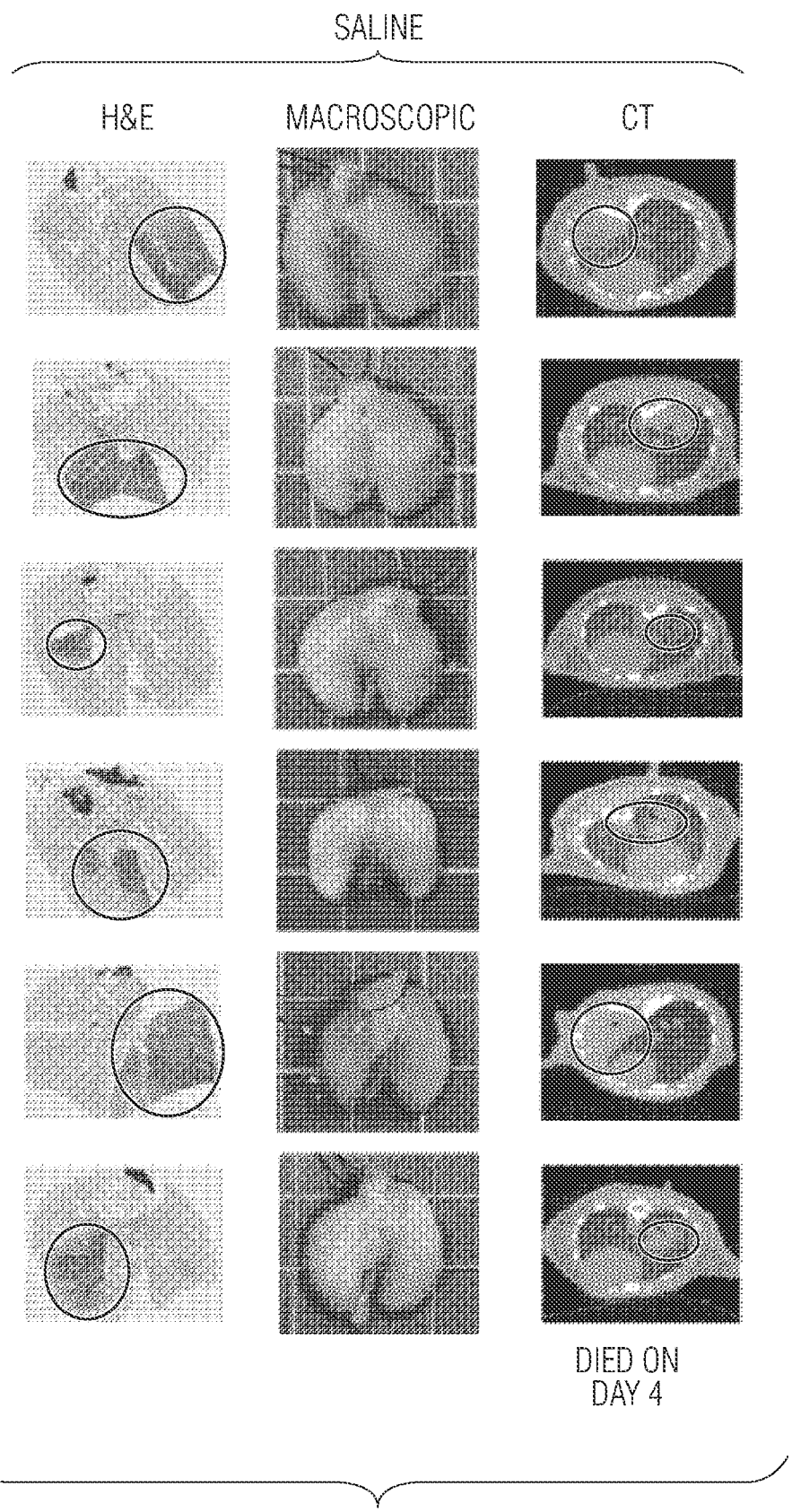
FIG. 11A shows a placebo control group (saline treatment) where the upper panels show CT scan of lungs in survived animals, the middle panels show a macroscopic picture of lungs, and the lower panels show H&E staining of lungs, according to an exemplary embodiment of the present disclosure.
Figure 11B:
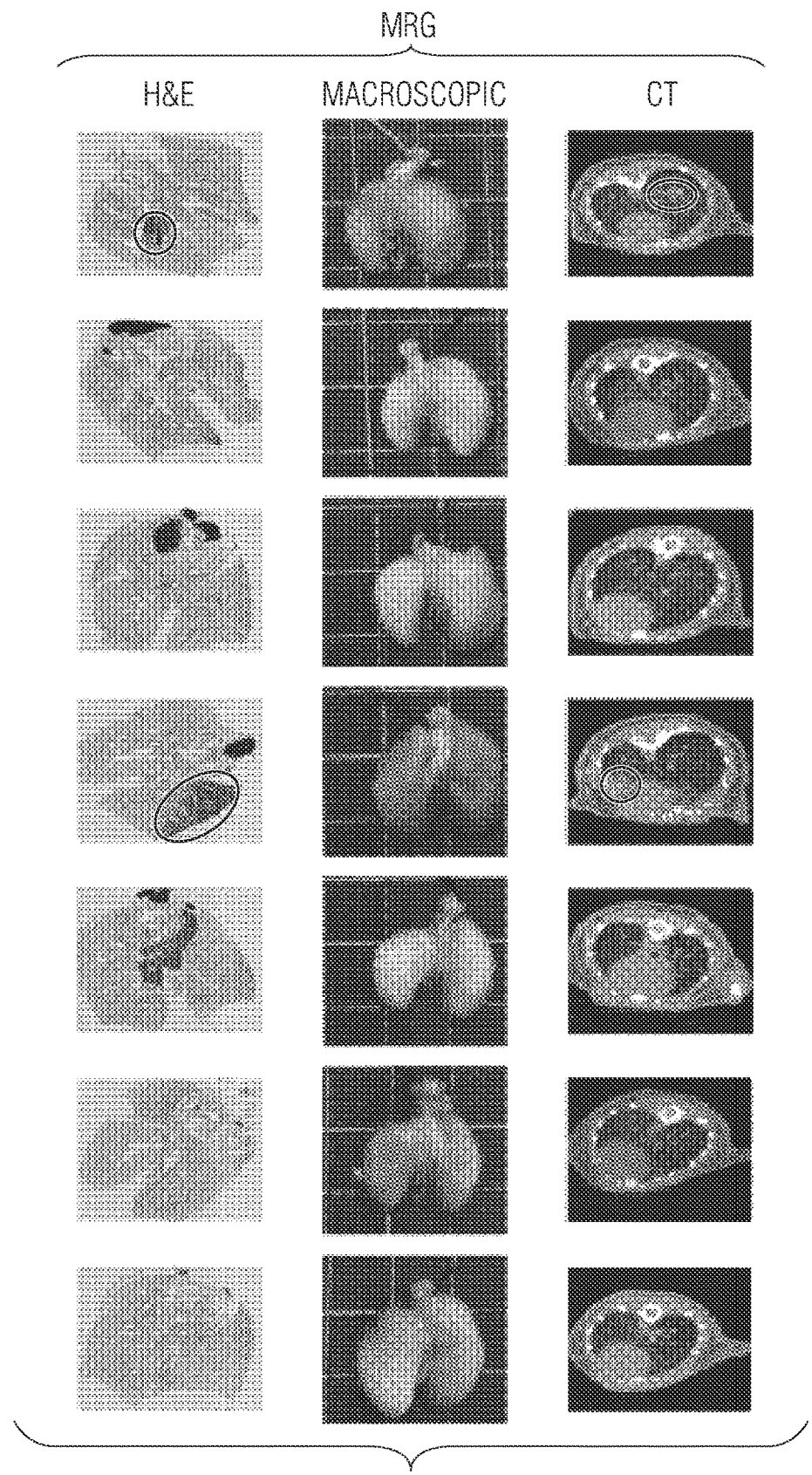
FIG. 11B shows a Formulation A treated group where the upper panels show CT scan of lungs in survived animals, the middle panels show a macroscopic picture of lungs and the lower panels show H&E staining of lungs.

FIGS. 11A and 11B demonstrate that Formulation A ameliorated lobar pneumococcal and reduced inflammation on mine on day 5 post intratracheal installation of *Strep. pneumoniae*. FIG. 11A shows a placebo control group. The upper panels of FIG. 11A show CT scan of lungs in survived animals the middle panels show a macroscopic picture of lungs, and the lower panels show H&E staining of lungs. FIG. 11B shows a Formulation A treated group. The upper panels of FIG. 11B show CT scan of lungs in survived animals, the middle panels show a macroscopic picture of lungs and the lower panels show H&E staining of lungs.

On day 5 post infection, CT scans of the lungs in all surviving mice in the placebo control group (6 out of 7) showed a focal dense opacification of the majority of an entire lobe with relative sparing of the large airways and/or ground-glass opacity in a lobar or segmental pattern (FIG. 11A, upper panels) suggesting the lobe pneumococcal pneumonia. In contrast, only 2 out of 7 mice treated with Formulation A showed a focal dense opacification of the majority or part of an entire lobe (FIG. 11B, upper panels). In a macroscopic picture of lungs from the same animals in the placebo control group: 5 animals showed spread/diffuse inflammation in both lungs, 1 animal showed limited patch lesions in both lungs and 1 animal with severe lung damage died at day 4 (FIG. 11A, middle panels). However, in the Formulation A treated group, 3 animals' lungs were almost fully recovered, and 2 animals' lungs showed a limited patch lesion in a lobe, and only 2 animals showed diffuse inflammation in both lungs (FIG. 11B, middle panels). H&E staining demonstrated an acute inflammation of entire or majority of lobe or lung in the placebo control group (FIG. 11A, middle panels). In the Formulation A treated group, 2 mice showed an acute inflammation of majority or segment of lobe, and 5 other mice showed acute inflammation involving only small bronchioles and adjacent alveoli (FIG. 11B, lower panels)

Amelioration of Cytokine Storm by Formulation A in Mice Infected with *Strep. pneumoniae*

FIGS. 12A to 12F show Formulation A ameliorated cytokine storm induced by *Strep. pneumoniae* infection in mice. Peripheral blood serum was collected at day 5 post infection and cytokine levels were measured by ELISA.

Figure 12A:
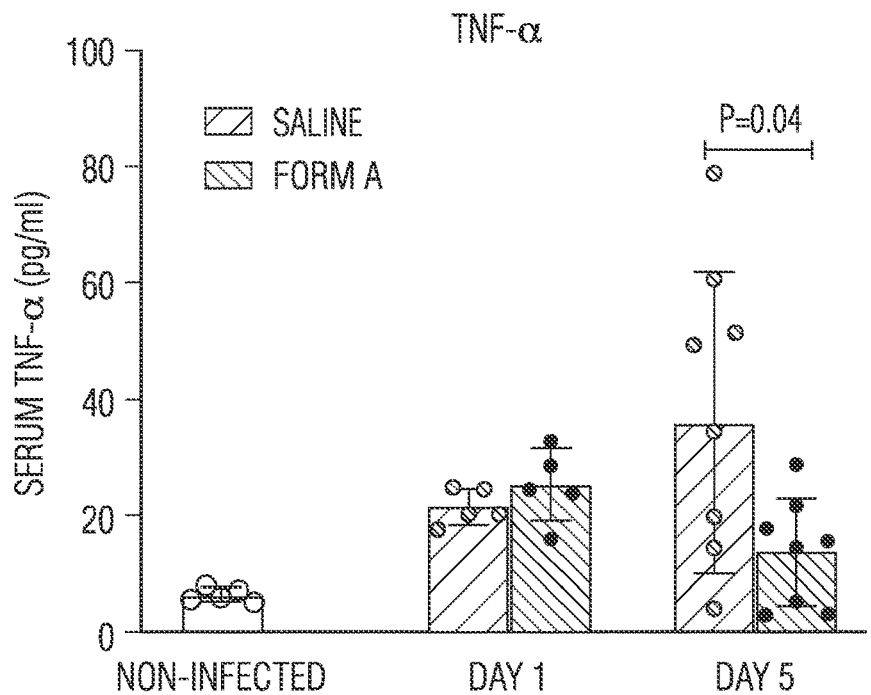
FIG. 12A shows serum TNF-α levels post-saline treatment or Formulation A treatment, according to an exemplary embodiment of the present disclosure.
Figure 12B:
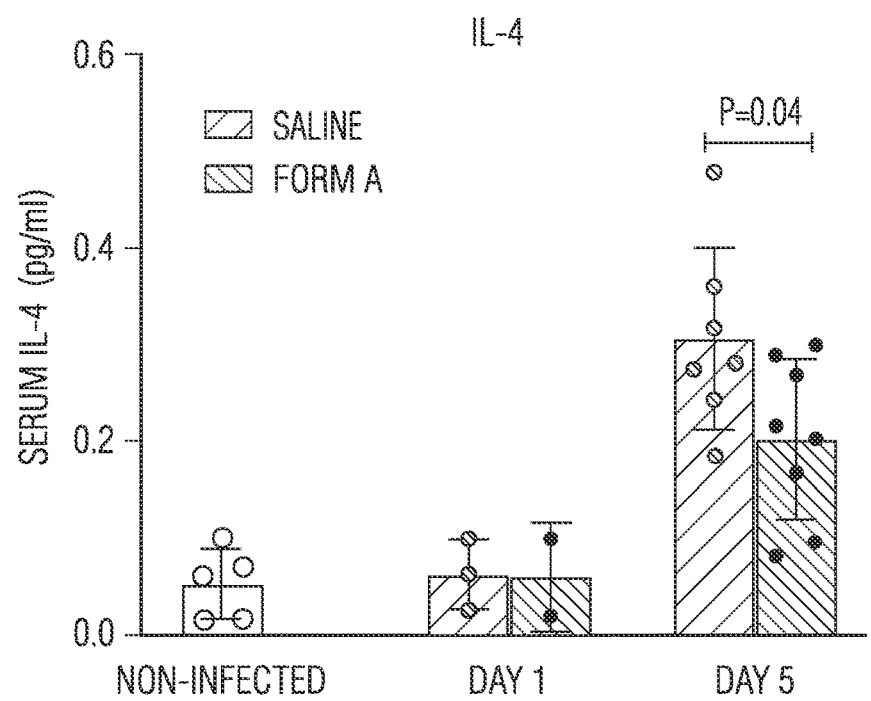
FIG. 12B shows serum IL-4 levels post-saline treatment or Formulation A treatment, according to an exemplary embodiment of the present disclosure.
Figure 12C:
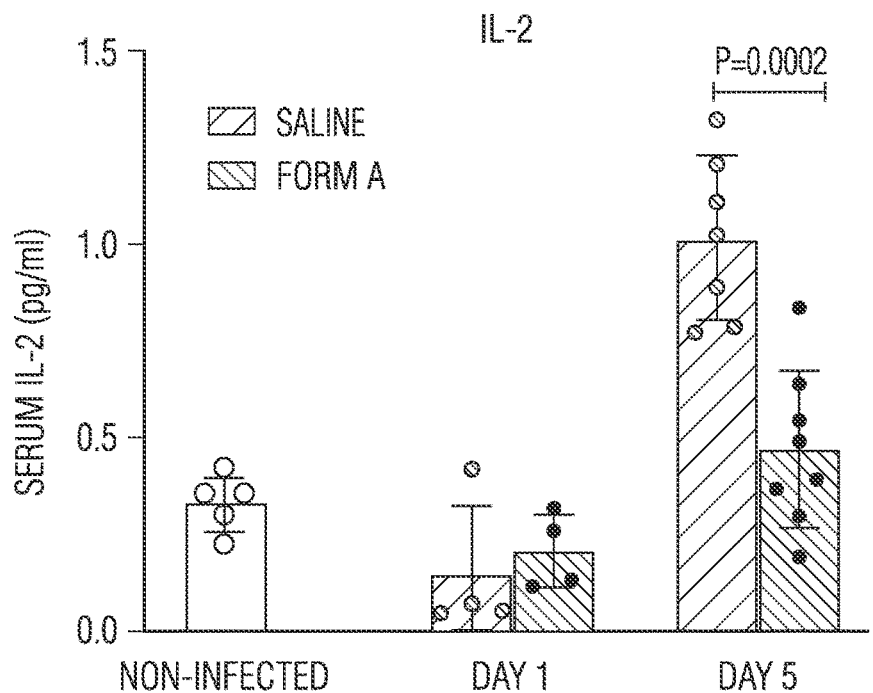
FIG. 12C shows serum IL-2 levels post-saline treatment or Formulation A treatment, according to an exemplary embodiment of the present disclosure.
Figure 12D:
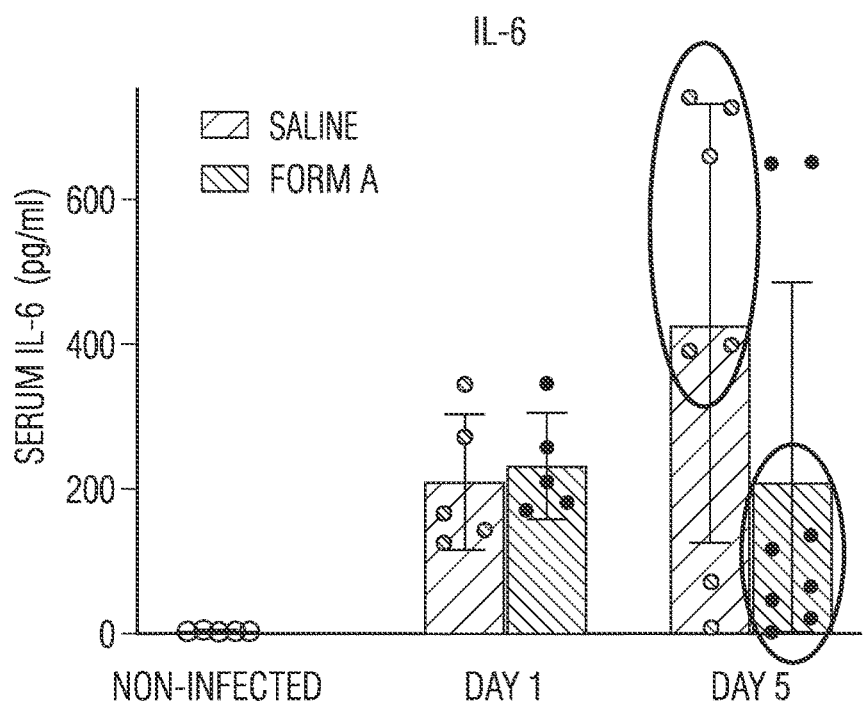
FIG. 12D shows serum IL-6 levels post-saline treatment or Formulation A treatment, according to an exemplary embodiment of the present disclosure.
Figure 12E:
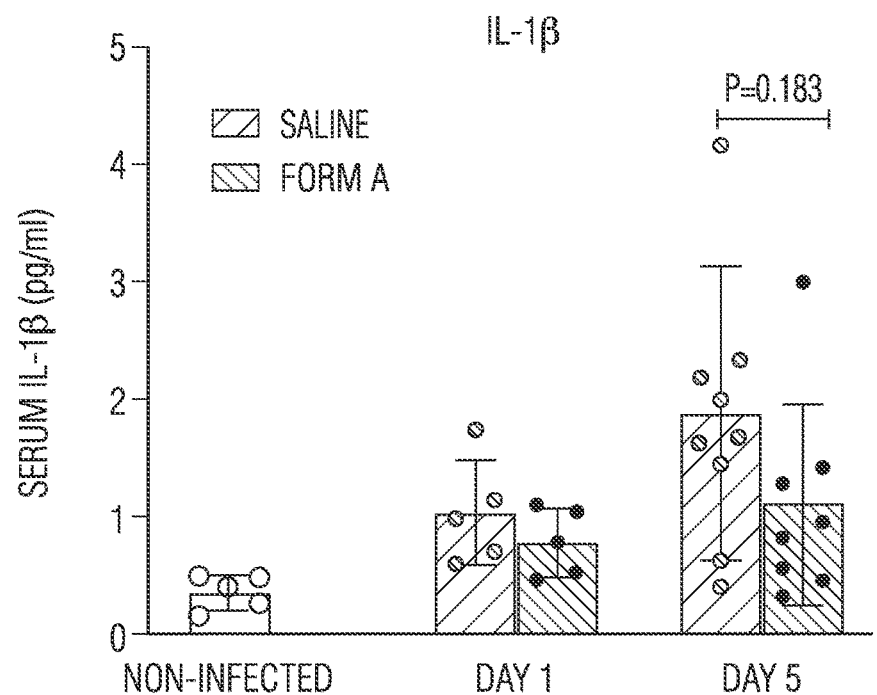
FIG. 12E shows serum IL-1β levels post-saline treatment or Formulation A treatment, according to an exemplary embodiment of the present disclosure.
Figure 12F:
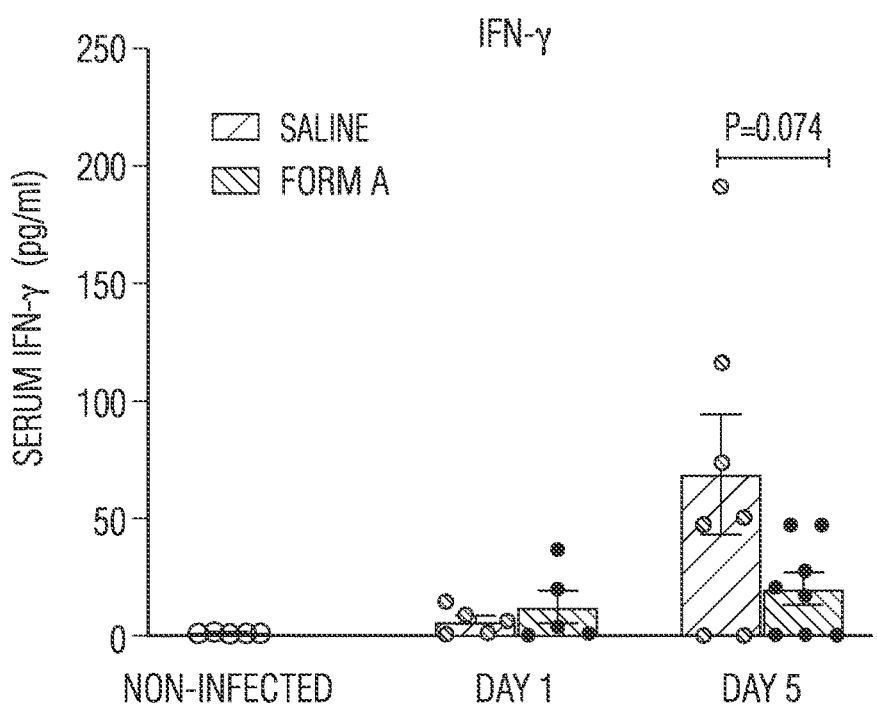
FIG. 12F shows serum IFN-γ levels post-saline treatment or Formulation A treatment, according to an exemplary embodiment of the present disclosure.

To determine if *Strep. pneumoniae* infection caused 'cytokine storm', several important cytokines in serum were measured from mice on day 5 post infection using ELISA. In controls, serum levels of TNF-a, IL-6 and IL-1beta were increased at 24 hours and along with other cytokines including IL-2, IL-4 and IFN-r reached peak levels at day 5 post infection (FIG. 12A to 12F), suggesting cytokine storms related to the lung infection. Formulation A treatment significantly reduced serum levels of TNF-a, IL-2 and IL-4 (FIGS. 12A, 12B and 12C). Although no statistical difference was observed in serum levels of IL-6 between control and Formulation A groups at day 5 post infection, 5 out of 7 animals in the placebo control group exhibited higher levels of IL-6, while 6 out of 8 treated animals showed lower levels of IL-6 compared to that at 24 hours (FIG. 12D, circle)

Formulation A Reduced Serum LDH Levels and Ameliorated Liver Injury

Figure 13A:
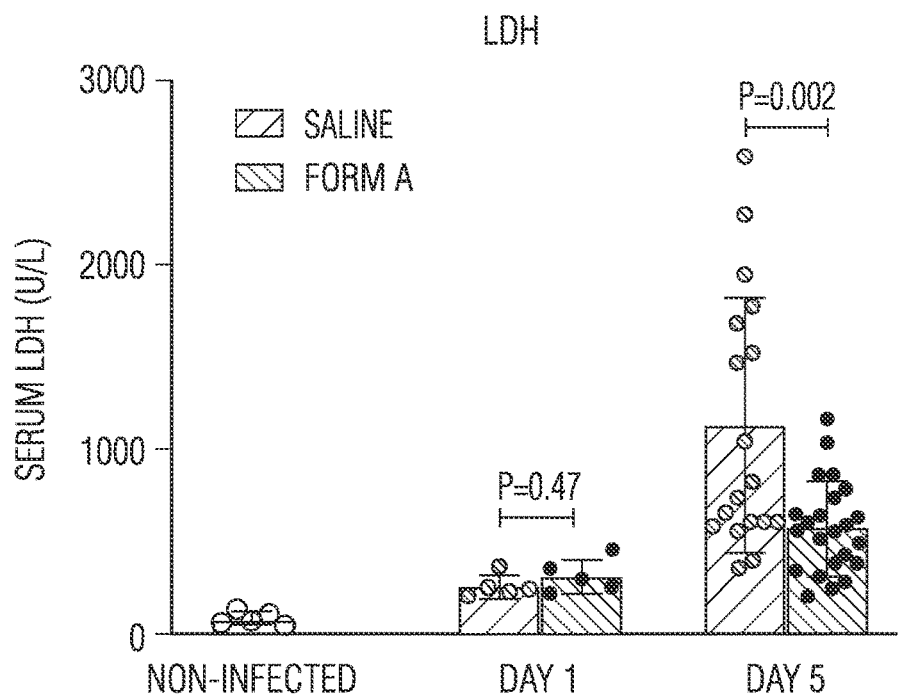
FIG. 13A shows serum lactate dehydrogenase (LDH) levels post-saline treatment or Formulation A treatment, according to an exemplary embodiment of the present disclosure.
Figure 13B:
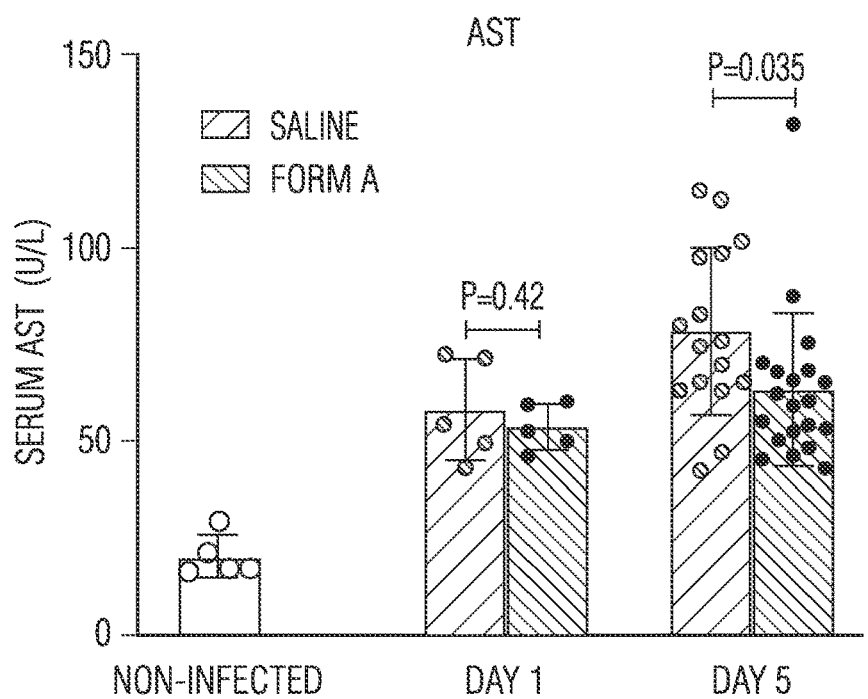
FIG. 13B shows aspartate aminotransferase (AST) levels post-saline treatment or Formulation A treatment, according to an exemplary embodiment of the present disclosure.
Figure 13C:
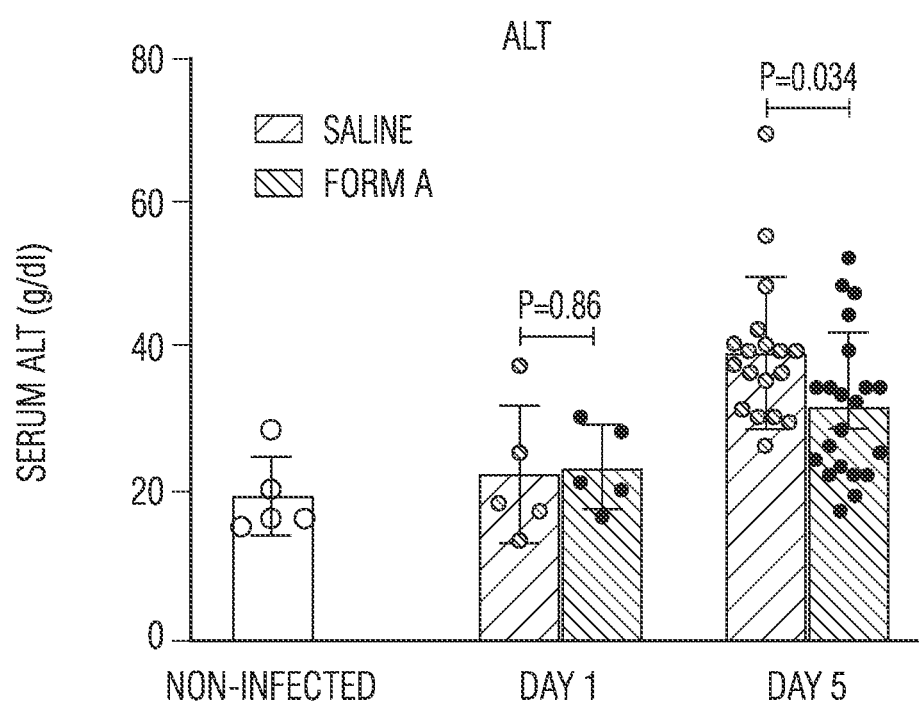
FIG. 13C shows alanine aminotransferase (ALT) levels post-saline treatment or Formulation A treatment, according to an exemplary embodiment of the present disclosure, according to an exemplary embodiment of the present disclosure.

FIGS. 13A to 13C shows Formulation A reduced serum LDH and ameliorated liver injury. Infected mice were sacrificed on day 1 or day 5. Blood chemistry tests were performed. FIG. 13A shows results for serum lactate dehydrogenase (LDH), FIG. 13B shows results for aspartate aminotransferase (AST), and Figure (C) shows results for alanine aminotransferase (ALT).

Lactate dehydrogenase (LDH) is an enzyme involved in energy production that is found in almost all of the body's cells, with the highest levels found in the cells of the lungs, heart, liver, muscles, kidneys, and in blood cells. When these tissues are damaged, they release LDH into the bloodstream. LDH is most often used to detect tissue damage. An additional 42 mice were studied for serum LDH levels at day 5 post infection. Notably all animals in the Formulation A group (n=21) survived, but in the placebo control group 1 mouse died on Day 3, and 1 mouse died on day 5. Blood serum levels of LDH were increased to about 1200 U/L in animals treated with saline at day 5 post infection (FIG. 13A). The blood levels of LDH were lowered to 640 U/L following Formulation A treatment. In addition, liver enzyme AST and ALT were also increased in infected test mice, but serum levels of AST and ALT were significantly lower in the Formulation A treatment group compared to placebo control group at day 5 post infection (FIGS. 13B and 13C).

Increased plasma levels of LDH have been associated with worse outcomes in COVID-19 infected patients. Published studies have reported that elevated LDH levels are associated with a 6-fold increase in the odds of developing severe disease and a 16-fold increase in odds of mortality in patients with COVID-19. Elevated LDH may also be an independent risk factor for exacerbation in mild COVID-19 patients. This study demonstrates that Formulation A treatment not only increased the number of stem cells in the injured lungs but also reduced tissue damage.

Recruitment of CD133+ Stem Cells and Ym1/2+CD68+ M2 Macrophages in Injured Lungs by Formulation A Treatment.

Figure 14A:
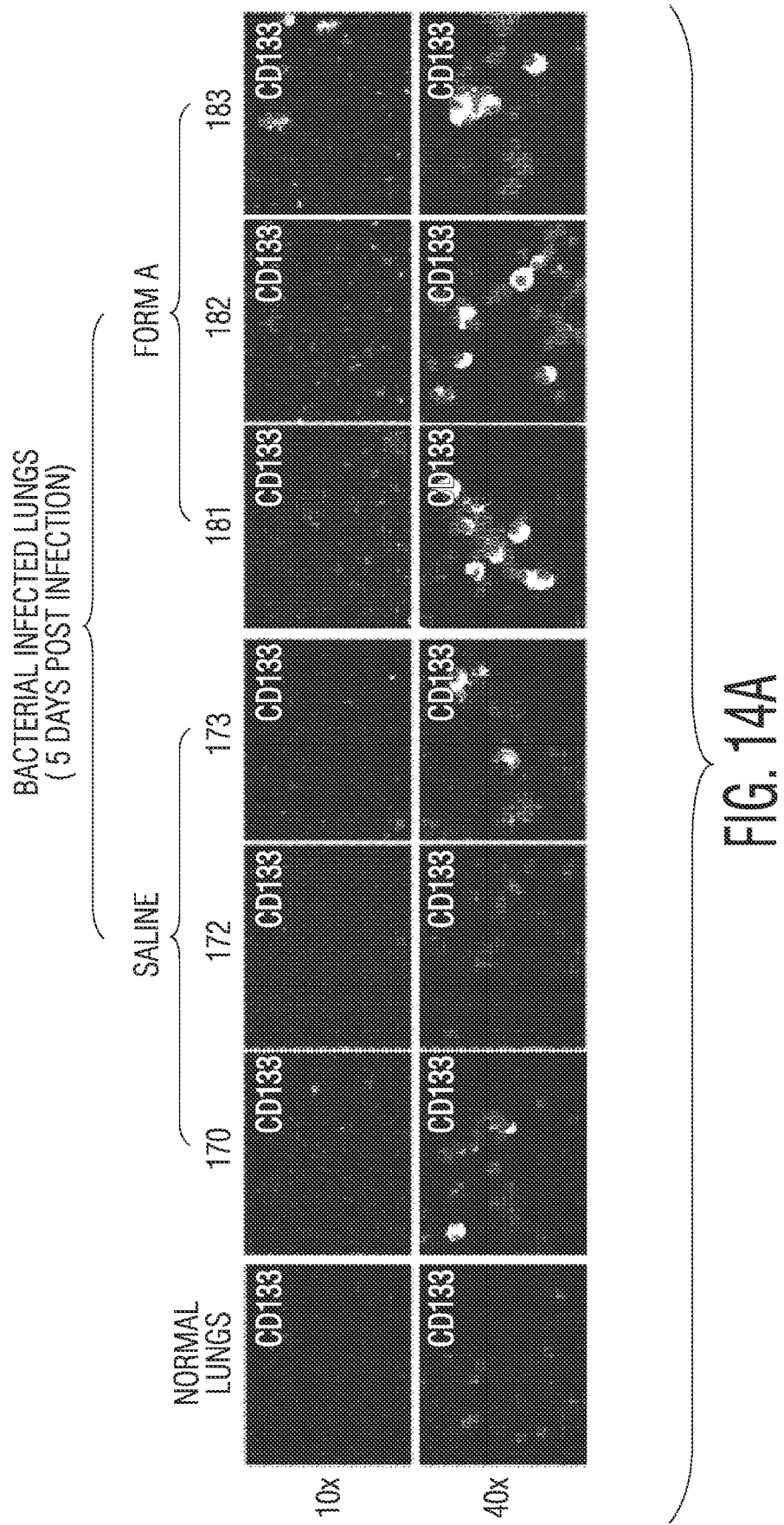
FIG. 14A shows immunofluorescence staining of cytospin slides of isolated lung cells 5 days post infection, according to an exemplary embodiment of the present disclosure.
Figure 14B:
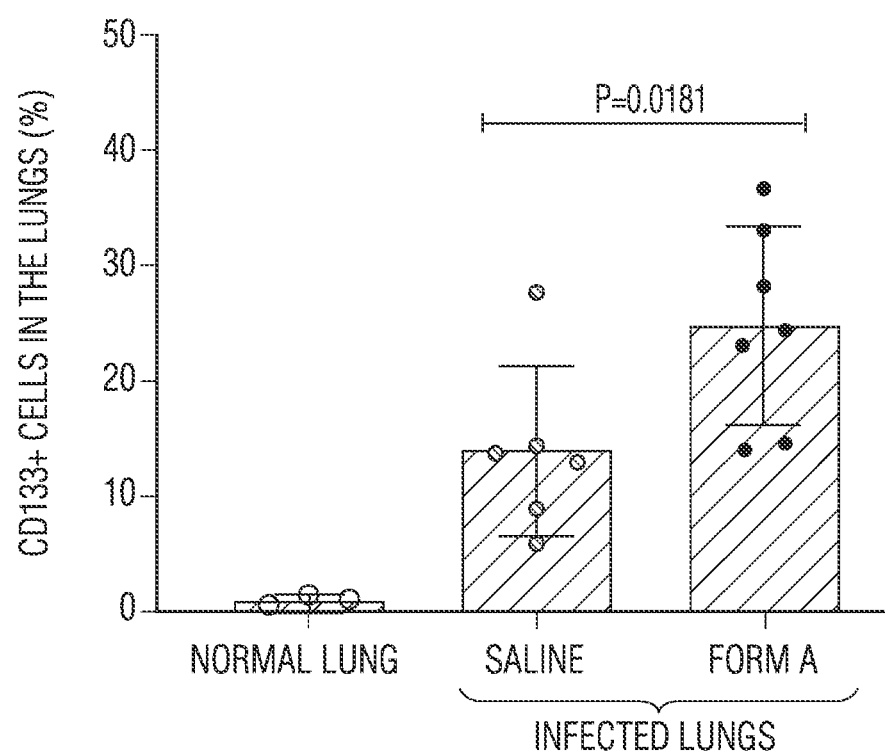
FIG. 14B shows percent of CD133+ cells in normal lung, lung treated with saline and lung treated with Formulation A, according to an exemplary embodiment of the present disclosure.

FIGS. 14A and 14B demonstrates that Formulation A increased CD133+ Stem Cells in the Injured Lung at Day 5 Following *Strep. pneumoniae* Infection. Cytospin slides of isolated lung cells from infected mice were stained with CD133 antibodies (green). 4',6-diamidino-2-phenylindole (DAPI) staining (blue) was used to determine the number of nuclei. CD133+ stem cells were identified in the lung cells recovered from mice treated with saline. CD133+ stem cells were significantly increased in the lung cells isolated from mice treated with Formulation A. Images are representative of 6 or 7 mice/group.

To determine if Formulation A treatment increases CD133+(progenitor) stem cells in injured lungs, animals were sacrificed on Day 5 and blood and lung tissue samples were collected. Lung cells were isolated by using collagenase digestion. Cytospin slides of isolated lung cells were stained with CD133 antibodies. Few CD133+ stem cells were identified in the normal lungs without injury. Immunofluorescence staining of cytospin slides of isolated lung cells showed that the number of CD133+ cells was increased in lung cells recovered from infected mice treated with saline which indicated a natural but inadequate process for recruiting stem cells after lung injury (FIGS. 14A and 14B). Unexpectedly, CD133+ cells were significantly more numerous in isolated lung cells in the animals receiving Formulation A treatment at Day 5 after infection. Some of these CD133+ cells exhibited a double nucleus which may indicate proliferation.

Figure 15:
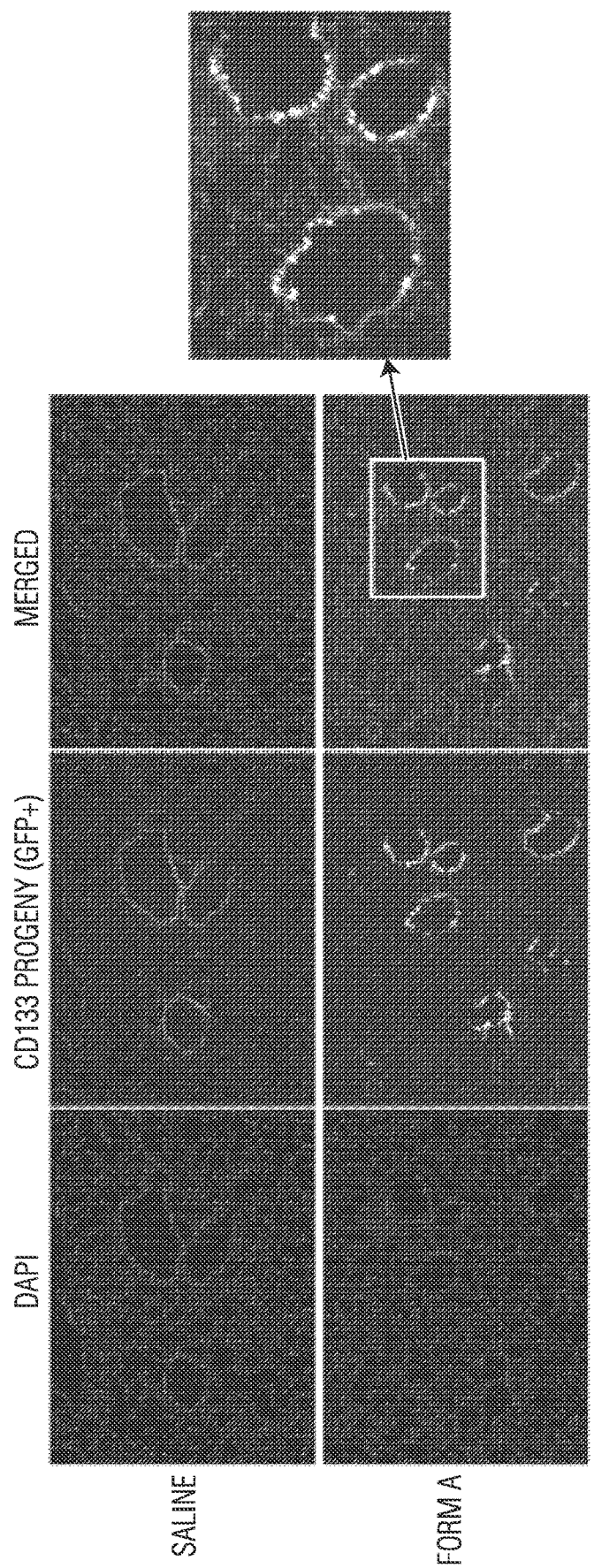
FIG. 15 shows generation of bronchial epithelium by CD133+ stem cells in the *Strep. pneumoniae* infected CD133+/C-L mice with Formulation A treatment, according to an exemplary embodiment of the present disclosure.

Lineage Tracing Demonstrated the Critical Role of CD133 Stem Cells in Improving Bronchial Airway Epithelium Healing by the Formulation A FIG. 15 shows CD133+ stem cells generate bronchial epithelium in the *Strep. pneumoniae* infected CD133+/C-L mice with Formulation A treatment. Injured lung tissues showed marked GFP expression in the bronchioles. Some of bronchial epithelial cells were repopulated by GFP-positive CD133 progeny cells (right panel).

Lineage tracing studies were performed to confirm the critical role of CD133 stem cells in healing of the injured lungs. Adult CD133 positive-Cre-nuclear(n)LacZ (CD133+/C-L) mice containing the Rosa26GFP reporter allele (CD133+/C-LxmTmG offspring) were infected with Strep. pneumoniae through intratracheal instillation of $4.5 \times 10^6$ CFU Streptococcus pneumoniae. Infected animals were randomly divided into two groups and received placebo or Formulation A (0.1 ml/kg) treatment at 24 hours after infection and every other day until day 28. CreERT2 activity was induced with tamoxifen 5 days before sacrificing (FIG. 10A). In this mouse model, the CD133 progeny were GFP positive.

GFP-positive cells were not observed in the lungs of non-infected or control treated mice (FIG. 15). However, in Formulation A group mice, GFP-positive cells were found in some of bronchioles, specifically in bronchial epithelium (FIG. 15). These results suggest that pharmacologically mobilized CD133 stem cells and their progeny are the principal contributors to bronchial epithelium regeneration. Airway epithelial cells are one of the earliest cell types infected in COM-19 patients, and immune-mediated epithelium damage correlates with COVID19 severity (9). Repairing and/or replacing damaged bronchial epithelial cells with pharmacologically mobilized CD133 stem cells may improve the recovery and prevent chronic pulmonary dysfunction.

Formulation A treatment in mice significantly reduced mortality rate by 75% (7% vs 28.2%) and improved survival (93% vs 71.8%) following acute lung injury and ARDS induced by intratracheal administration of Strep. pneumoniae. Together, these data demonstrated that Formulation A treatment reduced organ tissue damages and improved survival in Strep. pneumoniae infected mice with ARDS. Pharmacologically mobilized stem cells and activated M2 phenotype macrophages may not only ameliorate inflammatory immune response and cytokine storm, but also promote lung repair/regeneration Example 9: Formulation A as an Immunoregulatory and Regenerative Therapy for Arthritis Arthritis is the swelling and tenderness of one or more joints and usually involves inflammation or degeneration (breakdown) of joints. Arthritis is the most common cause of disability in the U.S. About 50 million adults and 300,000 children manage some form of arthritis.

Figure 16:
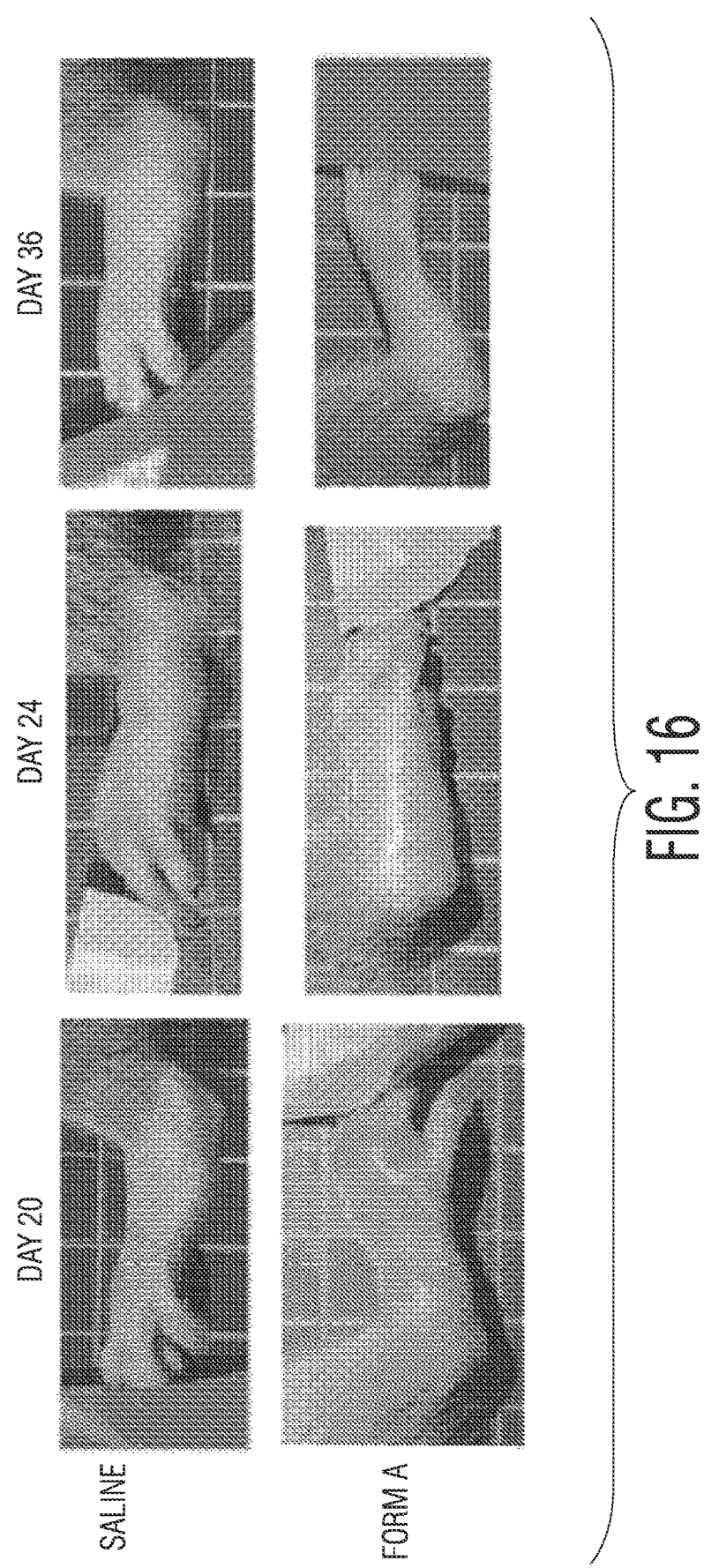
FIG. 16 shows photographs of clinical signs of arthritis in collagen-induced arthritis rats after treatment with Formulation A over time, according to an exemplary embodiment of the present disclosure.

FIG. 16 demonstrates that Formulation A treatment ameliorated the clinical signs of arthritis in collagen-induced arthritis rats. To test if MRG-001 can ameliorates inflammation of joints; a collagen-induced arthritis model in rats was developed. Collagen-Induced Arthritis (CIA) is a complex model of autoimmune-mediated arthritis that is regulated by multiple genetic and environmental factors. CIA is induced in rats by immunization with native type II collagen and develops joint pathology similar to that of rheumatoid arthritis.

Female DA rats aged 12-15 weeks, were immunized with type II collagen/Freund's incomplete adjuvant through intradermal injection (day 0) at three sites at the base of the tail using a latex-free 1 ml syringe and a 27-gauge needle, and lipopolysaccharides (LPS, 3 mg/kg) was given via Intraperitoneal injection on day 12 to boost immune response. Animals developed arthritis over next five day. Rats with arthritis were randomly divided into two experimental groups on day 20 and received saline or Formulation A subcutaneous injection every other day for 20 days.

Immunization induced an erosive arthritis of the hind paws. Macroscopic evidence of CIA first appeared as periarticular erythema and edema in the hind paws by days 17-20 after the first injection, with a 100% incidence by days 24. The hind paws remained erythema and edema by day 36 in rats treated with saline. In contrast, treatment with Formulation A with starting at the onset of arthritis (day 20) ameliorated the clinical signs on days 24-36 and improved hind paw activities. Thus, this study demonstrates that Formulation A can be used treat or ameliorate arthritis in patients.

While the present disclosure has been discussed in terms of certain embodiments, it should be appreciated that the present disclosure is not so limited. The embodiments are explained herein by way of example, and there are numerous modifications, variations and other embodiments that may be employed that would still be within the scope of the present disclosure.

The invention claimed is:

1. A pharmaceutical formulation comprising:
AMD3100 or a stem cell mobilizer;
Tacrolimus or a FK506 derivative or analog; and
one or more excipients, wherein the AMD3100 or stem cell mobilizer is in a concentration of about 16 to about 48 mg/mL, and
wherein the Tacrolimus or FK506 derivative or analog is in a concentration of about 0.3 to about 1.6 mg/mL.

2. The pharmaceutical formulation of claim 1, wherein the excipients comprise one or more of 1-N-Methly-2-Pyrrolidone (NMP), glycerin, dehydrated ethanol, sodium chloride, water for injection, hydrochloric acid, and sodium hydroxide.

3. The pharmaceutical formulation of claim 2, wherein the NMP is in a concentration of about 200 to about 450 mg/mL.

4. The pharmaceutical formulation of claim 2, wherein the glycerin is in a concentration of about 150 to about 350 mg/mL.

5. The pharmaceutical formulation of claim 2, wherein the dehydrated ethanol is in a concentration of about 20 to about 70 mg/mL.

6. The pharmaceutical formulation of claim 2, wherein the sodium chloride is in a concentration of about 1 to about 3 mg/mL.

7. The pharmaceutical formulation of claim 1, wherein the formulation is stable at room temperature for at least 10 days or under 2 to 8 degrees Celsius or about minus 20 degrees Celsius for at least 9 months.

8. The pharmaceutical formulation of claim 1, wherein the formulation is suitable for single dose subcutaneous injection.

9. A kit comprising at least one dosage form of the pharmaceutical formulations of claim 1 and instructions for administering the at least one dosage form to a subject or patient in need thereof.

* * * * *